(12) United States Patent
Viswanathan

(10) Patent No.: US 10,625,080 B1
(45) Date of Patent: Apr. 21, 2020

(54) SYSTEMS, APPARATUSES, AND METHODS FOR DETECTING ECTOPIC ELECTROCARDIOGRAM SIGNALS DURING PULSED ELECTRIC FIELD ABLATION

(71) Applicant: Farapulse, Inc., Menlo Park, CA (US)

(72) Inventor: Raju Viswanathan, Mountain View, CA (US)

(73) Assignee: Farapulse, Inc., Menlo Park, CA (US)

( * ) Notice: Subject to any disclaimer, the term of this patent is extended or adjusted under 35 U.S.C. 154(b) by 0 days.

(21) Appl. No.: 16/573,704

(22) Filed: Sep. 17, 2019

(51) Int. Cl.
| | | |
|---|---|---|
| *A61N 1/37* | (2006.01) | |
| *A61B 5/0456* | (2006.01) | |
| *A61N 1/365* | (2006.01) | |
| *A61B 5/00* | (2006.01) | |
| *A61B 5/04* | (2006.01) | |
| *A61B 5/0468* | (2006.01) | |

(52) U.S. Cl.
CPC .......... *A61N 1/371* (2013.01); *A61B 5/04017* (2013.01); *A61B 5/0456* (2013.01); *A61B 5/0468* (2013.01); *A61B 5/7257* (2013.01); *A61N 1/365* (2013.01)

(58) Field of Classification Search
CPC ........................... A61N 1/371; A61B 5/04017
USPC ........................................................ 600/510
See application file for complete search history.

(56) References Cited

U.S. PATENT DOCUMENTS

| | | |
|---|---|---|
| 4,200,104 A | 4/1980 | Harris |
| 4,470,407 A | 9/1984 | Hussein |
| 4,739,759 A | 4/1988 | Rexroth et al. |
| 5,234,004 A | 8/1993 | Hascoet et al. |
| 5,242,441 A | 9/1993 | Avitall |
| 5,257,635 A | 11/1993 | Langberg |
| 5,281,213 A | 1/1994 | Milder et al. |

(Continued)

FOREIGN PATENT DOCUMENTS

| | | |
|---|---|---|
| EP | 1042990 A1 | 10/2000 |
| EP | 1125549 | 8/2001 |

(Continued)

OTHER PUBLICATIONS

Partial Supplementary European Search Report for European Application No. 13827672.0, dated Mar. 23, 2016, 6 pages.

(Continued)

*Primary Examiner* — Nadia A Mahmood
(74) *Attorney, Agent, or Firm* — Cooley LLP

(57) ABSTRACT

Systems, apparatus, and methods for ablation therapy are described herein, with a processor for confirming pacing capture or detecting ectopic beats. An apparatus includes a processor for receiving cardiac signal data captured by a set of electrodes, extracting a sliding window of the cardiac signal data, identifying a peak frequency over a subrange of frequencies associated with the extracted sliding window, detecting ectopic activity based at least on a measure of the peak frequency over the subrange of frequencies, in response to detecting ectopic activity, sending an indication of ectopic activity to a signal generator configured to generate pulsed waveforms for cardiac ablation such that the signal generator is deactivated or switched off from generating the pulsed waveforms. An apparatus can further include a processor for confirming pacing capture of the set of pacing pulses based on cardiac signal data.

25 Claims, 10 Drawing Sheets

(56) References Cited

U.S. PATENT DOCUMENTS

| | | |
|---|---|---|
| 5,304,214 A | 4/1994 | DeFord et al. |
| 5,306,296 A | 4/1994 | Wright et al. |
| 5,334,193 A | 8/1994 | Nardella |
| 5,341,807 A | 8/1994 | Nardella |
| 5,342,301 A | 8/1994 | Saab |
| 5,398,683 A | 3/1995 | Edwards et al. |
| 5,443,463 A | 8/1995 | Stern et al. |
| 5,454,370 A | 10/1995 | Avitall |
| 5,515,848 A | 5/1996 | Corbett, III et al. |
| 5,531,685 A | 7/1996 | Hemmer et al. |
| 5,545,161 A | 8/1996 | Imran |
| 5,578,040 A | 11/1996 | Smith |
| 5,617,854 A | 4/1997 | Munsif |
| 5,624,430 A | 4/1997 | Eton et al. |
| 5,667,491 A | 9/1997 | Pliquett et al. |
| 5,672,170 A | 9/1997 | Cho |
| 5,700,243 A | 12/1997 | Narciso, Jr. |
| 5,702,438 A | 12/1997 | Avitall |
| 5,706,823 A | 1/1998 | Wodlinger |
| 5,722,400 A | 3/1998 | Ockuly et al. |
| 5,722,402 A | 3/1998 | Swanson et al. |
| 5,749,914 A | 5/1998 | Janssen |
| 5,779,699 A | 7/1998 | Lipson |
| 5,788,692 A | 8/1998 | Campbell et al. |
| 5,810,762 A | 9/1998 | Hofmann |
| 5,833,710 A | 11/1998 | Jacobson |
| 5,836,874 A | 11/1998 | Swanson et al. |
| 5,836,942 A | 11/1998 | Netherly et al. |
| 5,836,947 A | 11/1998 | Fleischman et al. |
| 5,843,154 A | 12/1998 | Osypka |
| 5,849,028 A | 12/1998 | Chen |
| 5,863,291 A | 1/1999 | Schaer |
| 5,868,736 A | 2/1999 | Swanson et al. |
| 5,871,523 A | 2/1999 | Fleischman et al. |
| 5,876,336 A | 3/1999 | Swanson et al. |
| 5,885,278 A | 3/1999 | Fleischman et al. |
| 5,895,404 A | 4/1999 | Ruiz |
| 5,899,917 A | 5/1999 | Edwards et al. |
| 5,904,709 A | 5/1999 | Arndt et al. |
| 5,916,158 A | 6/1999 | Webster, Jr. |
| 5,916,213 A | 6/1999 | Haissaguerre et al. |
| 5,921,924 A | 7/1999 | Avitall |
| 5,928,269 A | 7/1999 | Alt |
| 5,928,270 A | 7/1999 | Ramsey, III |
| 6,002,955 A | 12/1999 | Willems et al. |
| 6,006,131 A | 12/1999 | Cooper et al. |
| 6,009,351 A | 12/1999 | Flachman |
| 6,014,579 A | 1/2000 | Pomeranz et al. |
| 6,029,671 A | 2/2000 | Stevens et al. |
| 6,033,403 A | 3/2000 | Tu et al. |
| 6,035,238 A | 3/2000 | Ingle et al. |
| 6,045,550 A | 4/2000 | Simpson et al. |
| 6,068,653 A | 5/2000 | LaFontaine |
| 6,071,274 A | 6/2000 | Thompson et al. |
| 6,071,281 A | 6/2000 | Burnside et al. |
| 6,074,389 A | 6/2000 | Levine et al. |
| 6,076,012 A | 6/2000 | Swanson et al. |
| 6,090,104 A | 7/2000 | Webster, Jr. |
| 6,096,036 A | 8/2000 | Bowe et al. |
| 6,113,595 A | 9/2000 | Muntermann |
| 6,119,041 A | 9/2000 | Pomeranz et al. |
| 6,120,500 A | 9/2000 | Bednarek et al. |
| 6,146,381 A | 11/2000 | Bowe et al. |
| 6,164,283 A | 12/2000 | Lesh |
| 6,167,291 A | 12/2000 | Barajas et al. |
| 6,171,305 B1 | 1/2001 | Sherman |
| 6,216,034 B1 | 4/2001 | Hofmann et al. |
| 6,219,582 B1 | 4/2001 | Hofstad et al. |
| 6,223,085 B1 | 4/2001 | Dann et al. |
| 6,231,518 B1 | 5/2001 | Grabek et al. |
| 6,245,064 B1 | 6/2001 | Lesh et al. |
| 6,251,107 B1 | 6/2001 | Schaer |
| 6,251,128 B1 | 6/2001 | Knopp et al. |
| 6,270,476 B1 | 8/2001 | Santoianni et al. |
| 6,272,384 B1 | 8/2001 | Simon et al. |
| 6,287,306 B1 | 9/2001 | Kroll et al. |
| 6,314,963 B1 | 11/2001 | Vaska et al. |
| 6,322,559 B1 | 11/2001 | Daulton et al. |
| 6,350,263 B1 | 2/2002 | Wetzig et al. |
| 6,370,412 B1 | 4/2002 | Armoundas et al. |
| 6,391,024 B1 | 5/2002 | Sun et al. |
| 6,447,505 B2 | 9/2002 | McGovern et al. |
| 6,464,699 B1 | 10/2002 | Swanson |
| 6,470,211 B1 | 10/2002 | Ideker et al. |
| 6,502,576 B1 | 1/2003 | Lesh |
| 6,503,247 B2 | 1/2003 | Swartz et al. |
| 6,517,534 B1 | 2/2003 | McGovern et al. |
| 6,527,724 B1 | 3/2003 | Fenici |
| 6,527,767 B2 | 3/2003 | Wang et al. |
| 6,592,581 B2 | 7/2003 | Bowe |
| 6,595,991 B2 | 7/2003 | Tollner et al. |
| 6,607,520 B2 | 8/2003 | Keane |
| 6,623,480 B1 | 9/2003 | Kuo et al. |
| 6,638,278 B2 | 10/2003 | Falwell et al. |
| 6,666,863 B2 | 12/2003 | Wentzel et al. |
| 6,669,693 B2 | 12/2003 | Friedman |
| 6,702,811 B2 | 3/2004 | Stewart et al. |
| 6,719,756 B1 | 4/2004 | Muntermann |
| 6,723,092 B2 | 4/2004 | Brown et al. |
| 6,728,563 B2 | 4/2004 | Rashidi |
| 6,743,225 B2 | 6/2004 | Sanchez et al. |
| 6,743,226 B2 | 6/2004 | Cosman et al. |
| 6,743,239 B1 | 6/2004 | Kuehn et al. |
| 6,764,486 B2 | 7/2004 | Natale |
| 6,780,181 B2 | 8/2004 | Kroll et al. |
| 6,805,128 B1 | 10/2004 | Pless |
| 6,807,447 B2 | 10/2004 | Griffin, III |
| 6,892,091 B1 | 5/2005 | Ben-Haim et al. |
| 6,893,438 B2 | 5/2005 | Hall et al. |
| 6,926,714 B1 | 8/2005 | Sra |
| 6,955,173 B2 | 10/2005 | Lesh |
| 6,960,206 B2 | 11/2005 | Keane |
| 6,960,207 B2 | 11/2005 | Vanney et al. |
| 6,972,016 B2 | 12/2005 | Hill, III et al. |
| 6,973,339 B2 | 12/2005 | Govari |
| 6,979,331 B2 | 12/2005 | Hintringer et al. |
| 6,984,232 B2 | 1/2006 | Vanney et al. |
| 6,985,776 B2 | 1/2006 | Kane et al. |
| 7,001,383 B2 | 2/2006 | Keidar |
| 7,041,095 B2 | 5/2006 | Wang et al. |
| 7,113,831 B2 | 9/2006 | Hooven |
| 7,171,263 B2 | 1/2007 | Darvish et al. |
| 7,182,725 B2 | 2/2007 | Bonan et al. |
| 7,195,628 B2 | 3/2007 | Falkenberg |
| 7,207,988 B2 | 4/2007 | Leckrone et al. |
| 7,207,989 B2 | 4/2007 | Pike, Jr. et al. |
| 7,229,402 B2 | 6/2007 | Diaz et al. |
| 7,229,437 B2 | 6/2007 | Johnson et al. |
| 7,250,049 B2 | 7/2007 | Roop et al. |
| 7,285,116 B2 | 10/2007 | de la Rama et al. |
| 7,285,119 B2 | 10/2007 | Stewart et al. |
| 7,326,208 B2 | 2/2008 | Vanney et al. |
| 7,346,379 B2 | 3/2008 | Eng et al. |
| 7,367,974 B2 | 5/2008 | Haemmerich et al. |
| 7,374,567 B2 | 5/2008 | Heuser |
| 7,387,629 B2 | 6/2008 | Vanney et al. |
| 7,387,630 B2 | 6/2008 | Mest |
| 7,387,636 B2 | 6/2008 | Cohn et al. |
| 7,416,552 B2 | 8/2008 | Paul et al. |
| 7,419,477 B2 | 9/2008 | Simpson et al. |
| 7,419,489 B2 | 9/2008 | Vanney et al. |
| 7,422,591 B2 | 9/2008 | Phan |
| 7,429,261 B2 | 9/2008 | Kunis et al. |
| 7,435,248 B2 | 10/2008 | Taimisto et al. |
| 7,513,896 B2 | 4/2009 | Orszulak |
| 7,527,625 B2 | 5/2009 | Knight et al. |
| 7,578,816 B2 | 8/2009 | Boveja et al. |
| 7,588,567 B2 | 9/2009 | Boveja et al. |
| 7,623,899 B2 | 11/2009 | Worley et al. |
| 7,678,108 B2 | 3/2010 | Chrisitian et al. |
| 7,681,579 B2 | 3/2010 | Schwartz |
| 7,771,421 B2 | 8/2010 | Stewart et al. |
| 7,805,182 B2 | 9/2010 | Weese et al. |
| 7,850,642 B2 | 12/2010 | Moll et al. |

(56) References Cited

U.S. PATENT DOCUMENTS

| | | |
|---|---|---|
| 7,850,685 B2 | 12/2010 | Kunis et al. |
| 7,857,808 B2 | 12/2010 | Oral et al. |
| 7,857,809 B2 | 12/2010 | Drysen |
| 7,869,865 B2 | 1/2011 | Govari et al. |
| 7,896,873 B2 | 3/2011 | Hiller et al. |
| 7,917,211 B2 | 3/2011 | Zacouto |
| 7,918,819 B2 | 4/2011 | Karmarkar et al. |
| 7,918,850 B2 | 4/2011 | Govari et al. |
| 7,922,714 B2 | 4/2011 | Stevens-Wright |
| 7,955,827 B2 | 6/2011 | Rubinsky et al. |
| 8,048,067 B2 | 11/2011 | Davalos et al. |
| 8,048,072 B2 | 11/2011 | Verin et al. |
| 8,100,895 B2 | 1/2012 | Panos et al. |
| 8,100,900 B2 | 1/2012 | Prinz et al. |
| 8,108,069 B2 | 1/2012 | Stahler et al. |
| 8,133,220 B2 | 3/2012 | Lee et al. |
| 8,137,342 B2 | 3/2012 | Crossman |
| 8,145,289 B2 | 3/2012 | Calabro' et al. |
| 8,147,486 B2 | 4/2012 | Honour et al. |
| 8,160,690 B2 | 4/2012 | Wilfley et al. |
| 8,175,680 B2 | 5/2012 | Panescu |
| 8,182,477 B2 | 5/2012 | Orszulak et al. |
| 8,206,384 B2 | 6/2012 | Falwell et al. |
| 8,206,385 B2 | 6/2012 | Stangenes et al. |
| 8,216,221 B2 | 7/2012 | Ibrahim et al. |
| 8,221,411 B2 | 7/2012 | Francischelli et al. |
| 8,226,648 B2 | 7/2012 | Paul et al. |
| 8,228,065 B2 | 7/2012 | Wirtz et al. |
| 8,235,986 B2 | 8/2012 | Kulesa et al. |
| 8,235,988 B2 | 8/2012 | Davis et al. |
| 8,251,986 B2 | 8/2012 | Chornenky et al. |
| 8,282,631 B2 | 10/2012 | Davalos et al. |
| 8,287,532 B2 | 10/2012 | Carroll et al. |
| 8,414,508 B2 | 4/2013 | Thapliyal et al. |
| 8,430,875 B2 | 4/2013 | Ibrahim et al. |
| 8,433,394 B2 | 4/2013 | Harley et al. |
| 8,449,535 B2 | 5/2013 | Deno et al. |
| 8,454,594 B2 | 6/2013 | Demarais et al. |
| 8,463,368 B2 | 6/2013 | Harlev et al. |
| 8,475,450 B2 | 7/2013 | Govari et al. |
| 8,486,063 B2 | 7/2013 | Werneth et al. |
| 8,500,733 B2 | 8/2013 | Watson |
| 8,535,304 B2 | 9/2013 | Sklar et al. |
| 8,538,501 B2 | 9/2013 | Venkatachalam et al. |
| 8,562,588 B2 | 10/2013 | Hobbs et al. |
| 8,568,406 B2 | 10/2013 | Harlev et al. |
| 8,571,635 B2 | 10/2013 | McGee |
| 8,571,647 B2 | 10/2013 | Harlev et al. |
| 8,585,695 B2 | 11/2013 | Shih |
| 8,588,885 B2 | 11/2013 | Hall et al. |
| 8,597,288 B2 | 12/2013 | Christian |
| 8,608,735 B2 | 12/2013 | Govari et al. |
| 8,628,522 B2 | 1/2014 | Ibrahim et al. |
| 8,632,534 B2 | 1/2014 | Pearson et al. |
| 8,647,338 B2 | 2/2014 | Chornenky et al. |
| 8,708,952 B2 | 4/2014 | Cohen et al. |
| 8,734,442 B2 | 5/2014 | Cao et al. |
| 8,771,267 B2 | 7/2014 | Kunis et al. |
| 8,795,310 B2 | 8/2014 | Fung et al. |
| 8,808,273 B2 | 8/2014 | Caples et al. |
| 8,808,281 B2 | 8/2014 | Emons et al. |
| 8,834,461 B2 | 9/2014 | Werneth et al. |
| 8,834,464 B2 | 9/2014 | Stewart et al. |
| 8,868,169 B2 | 10/2014 | Narayan et al. |
| 8,876,817 B2 | 11/2014 | Avitall et al. |
| 8,880,195 B2 | 11/2014 | Azure |
| 8,886,309 B2 | 11/2014 | Luther et al. |
| 8,903,488 B2 | 12/2014 | Callas et al. |
| 8,920,411 B2 | 12/2014 | Gelbart et al. |
| 8,926,589 B2 | 1/2015 | Govari |
| 8,932,287 B2 | 1/2015 | Gelbart et al. |
| 8,945,117 B2 | 2/2015 | Bencini |
| 8,979,841 B2 | 3/2015 | Kunis et al. |
| 8,986,278 B2 | 3/2015 | Fung et al. |
| 9,002,442 B2 | 4/2015 | Harley et al. |
| 9,005,189 B2 | 4/2015 | Davalos et al. |
| 9,005,194 B2 | 4/2015 | Oral et al. |
| 9,011,425 B2 | 4/2015 | Fischer et al. |
| 9,044,245 B2 | 6/2015 | Condie et al. |
| 9,055,959 B2 | 6/2015 | Vaska et al. |
| 9,072,518 B2 | 7/2015 | Swanson |
| 9,078,667 B2 | 7/2015 | Besser et al. |
| 9,101,374 B1 | 8/2015 | Hoch et al. |
| 9,119,533 B2 | 9/2015 | Ghaffari |
| 9,119,634 B2 | 9/2015 | Gelbart et al. |
| 9,131,897 B2 | 9/2015 | Harada et al. |
| 9,155,590 B2 | 10/2015 | Mathur |
| 9,162,037 B2 | 10/2015 | Belson et al. |
| 9,179,972 B2 | 11/2015 | Olson |
| 9,186,481 B2 | 11/2015 | Avitall et al. |
| 9,192,769 B2 | 11/2015 | Donofrio et al. |
| 9,211,405 B2 | 12/2015 | Mahapatra et al. |
| 9,216,055 B2 | 12/2015 | Spence et al. |
| 9,233,248 B2 | 1/2016 | Luther et al. |
| 9,237,926 B2 | 1/2016 | Nollert et al. |
| 9,262,252 B2 | 2/2016 | Kirkpatrick et al. |
| 9,277,957 B2 | 3/2016 | Long et al. |
| 9,282,910 B2 | 3/2016 | Narayan et al. |
| 9,289,258 B2 | 3/2016 | Cohen |
| 9,289,606 B2 | 3/2016 | Paul et al. |
| 9,295,516 B2 | 3/2016 | Pearson et al. |
| 9,301,801 B2 | 4/2016 | Scheib |
| 9,375,268 B2 | 6/2016 | Long |
| 9,414,881 B2 | 8/2016 | Callas et al. |
| 9,468,495 B2 | 10/2016 | Kunis et al. |
| 9,474,486 B2 | 10/2016 | Eliason et al. |
| 9,474,574 B2 | 10/2016 | Ibrahim et al. |
| 9,480,525 B2 | 11/2016 | Lopes et al. |
| 9,486,272 B2 | 11/2016 | Bonyak et al. |
| 9,486,273 B2 | 11/2016 | Lopes et al. |
| 9,492,227 B2 | 11/2016 | Lopes et al. |
| 9,492,228 B2 | 11/2016 | Lopes et al. |
| 9,517,103 B2 | 12/2016 | Panescu et al. |
| 9,526,573 B2 | 12/2016 | Lopes et al. |
| 9,532,831 B2 | 1/2017 | Reinders et al. |
| 9,539,010 B2 | 1/2017 | Gagner et al. |
| 9,554,848 B2 | 1/2017 | Stewart et al. |
| 9,554,851 B2 | 1/2017 | Sklar et al. |
| 9,700,368 B2 | 7/2017 | Callas et al. |
| 9,724,170 B2 | 8/2017 | Mickelsen |
| 9,757,193 B2 | 9/2017 | Zarins et al. |
| 9,782,099 B2 | 10/2017 | Williams et al. |
| 9,795,442 B2 | 10/2017 | Salahieh et al. |
| 9,861,802 B2 | 1/2018 | Mickelsen |
| 9,913,685 B2 | 3/2018 | Clark et al. |
| 9,931,487 B2 | 4/2018 | Quinn et al. |
| 9,987,081 B1 | 6/2018 | Bowers et al. |
| 9,999,465 B2 | 6/2018 | Long et al. |
| 10,016,232 B1 | 7/2018 | Bowers et al. |
| 10,130,423 B1 | 11/2018 | Viswanathan et al. |
| 10,172,673 B2 | 1/2019 | Viswanathan et al. |
| 10,322,286 B2 | 6/2019 | Viswanathan et al. |
| 10,433,906 B2 | 10/2019 | Mickelsen |
| 10,433,908 B2 | 10/2019 | Viswanathan et al. |
| 10,507,302 B2 | 12/2019 | Leeflang et al. |
| 10,512,505 B2 | 12/2019 | Viswanathan |
| 10,512,779 B2 | 12/2019 | Viswanathan et al. |
| 10,517,672 B2 | 12/2019 | Long |
| 2001/0000791 A1 | 5/2001 | Suorsa et al. |
| 2001/0007070 A1 | 7/2001 | Stewart et al. |
| 2001/0044624 A1 | 11/2001 | Seraj et al. |
| 2002/0052602 A1 | 5/2002 | Wang et al. |
| 2002/0077627 A1 | 6/2002 | Johnson et al. |
| 2002/0087169 A1 | 7/2002 | Brock et al. |
| 2002/0091384 A1 | 7/2002 | Hooven et al. |
| 2002/0095176 A1 | 7/2002 | Liddicoat et al. |
| 2002/0111618 A1 | 8/2002 | Stewart et al. |
| 2002/0156526 A1 | 10/2002 | Hlavka et al. |
| 2002/0161323 A1 | 10/2002 | Miller et al. |
| 2002/0169445 A1 | 11/2002 | Jain et al. |
| 2002/0177765 A1 | 11/2002 | Bowe et al. |
| 2002/0183638 A1 | 12/2002 | Swanson |
| 2003/0014098 A1 | 1/2003 | Quijano et al. |
| 2003/0018374 A1 | 1/2003 | Paulos |

(56) References Cited

U.S. PATENT DOCUMENTS

| | | |
|---|---|---|
| 2003/0023287 A1 | 1/2003 | Edwards et al. |
| 2003/0028189 A1 | 2/2003 | Woloszko et al. |
| 2003/0050637 A1 | 3/2003 | Maguire et al. |
| 2003/0114849 A1 | 6/2003 | Ryan |
| 2003/0125729 A1 | 7/2003 | Hooven et al. |
| 2003/0130598 A1 | 7/2003 | Manning et al. |
| 2003/0130711 A1 | 7/2003 | Pearson et al. |
| 2003/0204161 A1 | 10/2003 | Ferek Petric |
| 2003/0229379 A1 | 12/2003 | Ramsey |
| 2004/0039382 A1 | 2/2004 | Kroll et al. |
| 2004/0049181 A1 | 3/2004 | Stewart et al. |
| 2004/0049182 A1 | 3/2004 | Koblish et al. |
| 2004/0082859 A1 | 4/2004 | Schaer |
| 2004/0082948 A1 | 4/2004 | Stewart et al. |
| 2004/0087939 A1 | 5/2004 | Eggers et al. |
| 2004/0111087 A1 | 6/2004 | Stern et al. |
| 2004/0199157 A1 | 10/2004 | Palanker et al. |
| 2004/0215139 A1 | 10/2004 | Cohen |
| 2004/0231683 A1 | 11/2004 | Eng et al. |
| 2004/0236360 A1 | 11/2004 | Cohn et al. |
| 2004/0254607 A1 | 12/2004 | Wittenberger et al. |
| 2004/0267337 A1 | 12/2004 | Hayzelden |
| 2005/0033282 A1 | 2/2005 | Hooven |
| 2005/0187545 A1 | 8/2005 | Hooven et al. |
| 2005/0222632 A1 | 10/2005 | Obino |
| 2005/0251130 A1 | 11/2005 | Boveja et al. |
| 2005/0261672 A1 | 11/2005 | Deem et al. |
| 2006/0009755 A1 | 1/2006 | Sra |
| 2006/0009759 A1 | 1/2006 | Christian et al. |
| 2006/0015095 A1 | 1/2006 | Desinger et al. |
| 2006/0015165 A1 | 1/2006 | Bertolero et al. |
| 2006/0024359 A1 | 2/2006 | Walker et al. |
| 2006/0058781 A1 | 3/2006 | Long |
| 2006/0111702 A1 | 5/2006 | Oral et al. |
| 2006/0142801 A1 | 6/2006 | Demarais et al. |
| 2006/0167448 A1 | 7/2006 | Kozel |
| 2006/0217703 A1 | 9/2006 | Chornenky et al. |
| 2006/0241734 A1 | 10/2006 | Marshall et al. |
| 2006/0264752 A1 | 11/2006 | Rubinsky et al. |
| 2006/0270900 A1 | 11/2006 | Chin et al. |
| 2006/0287648 A1 | 12/2006 | Schwartz |
| 2006/0293730 A1 | 12/2006 | Rubinsky et al. |
| 2006/0293731 A1 | 12/2006 | Rubinsky et al. |
| 2007/0005053 A1 | 1/2007 | Dando |
| 2007/0021744 A1 | 1/2007 | Creighton |
| 2007/0060989 A1 | 3/2007 | Deem et al. |
| 2007/0066972 A1 | 3/2007 | Ormsby et al. |
| 2007/0129721 A1 | 6/2007 | Phan et al. |
| 2007/0129760 A1 | 6/2007 | Demarais et al. |
| 2007/0156135 A1 | 7/2007 | Rubinsky et al. |
| 2007/0167740 A1 | 7/2007 | Grunewald et al. |
| 2007/0167940 A1 | 7/2007 | Stevens-Wright |
| 2007/0173878 A1 | 7/2007 | Heuser |
| 2007/0208329 A1 | 9/2007 | Ward et al. |
| 2007/0225589 A1 | 9/2007 | Viswanathan |
| 2007/0249923 A1 | 10/2007 | Keenan |
| 2007/0260223 A1 | 11/2007 | Scheibe et al. |
| 2007/0270792 A1 | 11/2007 | Hennemann et al. |
| 2008/0009855 A1 | 1/2008 | Hamou |
| 2008/0033426 A1 | 2/2008 | Machell |
| 2008/0065061 A1 | 3/2008 | Viswanathan |
| 2008/0086120 A1 | 4/2008 | Mirza et al. |
| 2008/0091195 A1 | 4/2008 | Silwa et al. |
| 2008/0103545 A1 | 5/2008 | Bolea et al. |
| 2008/0132885 A1 | 6/2008 | Rubinsky et al. |
| 2008/0161789 A1 | 7/2008 | Thao et al. |
| 2008/0172048 A1 | 7/2008 | Martin et al. |
| 2008/0200913 A1 | 8/2008 | Viswanathan |
| 2008/0208118 A1 | 8/2008 | Goldman |
| 2008/0243214 A1 | 10/2008 | Koblish |
| 2008/0281322 A1 | 11/2008 | Sherman et al. |
| 2008/0300574 A1 | 12/2008 | Belson et al. |
| 2008/0300588 A1 | 12/2008 | Groth et al. |
| 2009/0024084 A1 | 1/2009 | Khosla et al. |
| 2009/0048591 A1 | 2/2009 | Ibrahim et al. |
| 2009/0062788 A1 | 3/2009 | Long et al. |
| 2009/0076500 A1 | 3/2009 | Azure |
| 2009/0105654 A1 | 4/2009 | Kurth et al. |
| 2009/0138009 A1 | 5/2009 | Viswanathan et al. |
| 2009/0149917 A1 | 6/2009 | Whitehurst et al. |
| 2009/0163905 A1 | 6/2009 | Winkler et al. |
| 2009/0228003 A1 | 9/2009 | Sinelnikov |
| 2009/0240248 A1 | 9/2009 | Deford et al. |
| 2009/0275827 A1 | 11/2009 | Aiken et al. |
| 2009/0281477 A1 | 11/2009 | Mikus et al. |
| 2009/0306651 A1 | 12/2009 | Schneider |
| 2010/0004623 A1 | 1/2010 | Hamilton et al. |
| 2010/0023004 A1 | 1/2010 | Francischelli et al. |
| 2010/0137861 A1 | 6/2010 | Soroff et al. |
| 2010/0185140 A1 | 7/2010 | Kassab et al. |
| 2010/0185186 A1 | 7/2010 | Longoria |
| 2010/0191112 A1 | 7/2010 | Demarais et al. |
| 2010/0191232 A1 | 7/2010 | Boveda |
| 2010/0241185 A1 | 9/2010 | Mahapatra et al. |
| 2010/0261994 A1 | 10/2010 | Davalos et al. |
| 2010/0274238 A1 | 10/2010 | Klimovitch |
| 2010/0280513 A1 | 11/2010 | Juergen et al. |
| 2010/0280539 A1 | 11/2010 | Miyoshi et al. |
| 2010/0292687 A1 | 11/2010 | Kauphusman et al. |
| 2010/0312096 A1 | 12/2010 | Guttman et al. |
| 2010/0312300 A1 | 12/2010 | Ryu et al. |
| 2011/0028962 A1 | 2/2011 | Werneth et al. |
| 2011/0028964 A1 | 2/2011 | Edwards |
| 2011/0040199 A1* | 2/2011 | Hopenfeld .......... A61B 5/0452 600/515 |
| 2011/0098694 A1 | 4/2011 | Long |
| 2011/0106221 A1 | 5/2011 | Neal, II et al. |
| 2011/0130708 A1 | 6/2011 | Perry et al. |
| 2011/0144524 A1 | 6/2011 | Fish et al. |
| 2011/0144633 A1 | 6/2011 | Govari |
| 2011/0160785 A1 | 6/2011 | Mori et al. |
| 2011/0190659 A1 | 8/2011 | Long et al. |
| 2011/0190727 A1 | 8/2011 | Edmunds et al. |
| 2011/0213231 A1 | 9/2011 | Hall et al. |
| 2011/0276047 A1 | 11/2011 | Sklar et al. |
| 2011/0276075 A1 | 11/2011 | Fung et al. |
| 2011/0288544 A1 | 11/2011 | Verin et al. |
| 2011/0288547 A1 | 11/2011 | Morgan et al. |
| 2011/0313417 A1 | 12/2011 | De La Rama et al. |
| 2012/0029512 A1 | 2/2012 | Willard et al. |
| 2012/0046570 A1 | 2/2012 | Villegas et al. |
| 2012/0053581 A1 | 3/2012 | Wittkampf et al. |
| 2012/0059255 A1 | 3/2012 | Paul et al. |
| 2012/0071872 A1 | 3/2012 | Rubinsky et al. |
| 2012/0078343 A1 | 3/2012 | Fish |
| 2012/0089089 A1 | 4/2012 | Swain et al. |
| 2012/0095459 A1 | 4/2012 | Callas et al. |
| 2012/0101413 A1 | 4/2012 | Beetel et al. |
| 2012/0158021 A1 | 6/2012 | Morrill |
| 2012/0165667 A1 | 6/2012 | Altmann et al. |
| 2012/0172859 A1 | 7/2012 | Condie et al. |
| 2012/0172867 A1 | 7/2012 | Ryu et al. |
| 2012/0197100 A1 | 8/2012 | Razavi et al. |
| 2012/0209260 A1 | 8/2012 | Lambert et al. |
| 2012/0220998 A1 | 8/2012 | Long et al. |
| 2012/0265198 A1 | 10/2012 | Crow et al. |
| 2012/0283582 A1 | 11/2012 | Mahapatra et al. |
| 2012/0303019 A1 | 11/2012 | Zhao et al. |
| 2012/0310052 A1 | 12/2012 | Mahapatra et al. |
| 2012/0310230 A1 | 12/2012 | Willis |
| 2012/0310237 A1 | 12/2012 | Swanson |
| 2012/0316557 A1 | 12/2012 | Sartor et al. |
| 2013/0030430 A1 | 1/2013 | Stewart et al. |
| 2013/0060247 A1 | 3/2013 | Sklar et al. |
| 2013/0060248 A1 | 3/2013 | Sklar et al. |
| 2013/0079768 A1 | 3/2013 | De Luca et al. |
| 2013/0090651 A1 | 4/2013 | Smith |
| 2013/0096655 A1 | 4/2013 | Moffitt et al. |
| 2013/0103027 A1 | 4/2013 | Sklar et al. |
| 2013/0103064 A1 | 4/2013 | Arenson et al. |
| 2013/0131662 A1 | 5/2013 | Wittkampf |
| 2013/0158538 A1 | 6/2013 | Govari |
| 2013/0158621 A1* | 6/2013 | Ding .................. A61B 5/0468 607/17 |

(56) References Cited

U.S. PATENT DOCUMENTS

| | | |
|---|---|---|
| 2013/0172864 A1 | 7/2013 | Ibrahim et al. |
| 2013/0172875 A1 | 7/2013 | Govari et al. |
| 2013/0184702 A1 | 7/2013 | Neal, II et al. |
| 2013/0218157 A1 | 8/2013 | Callas et al. |
| 2013/0226174 A1 | 8/2013 | Ibrahim et al. |
| 2013/0237984 A1 | 9/2013 | Sklar |
| 2013/0253415 A1 | 9/2013 | Sano et al. |
| 2013/0296679 A1 | 11/2013 | Condie et al. |
| 2013/0310829 A1 | 11/2013 | Cohen |
| 2013/0317385 A1 | 11/2013 | Sklar et al. |
| 2013/0331831 A1 | 12/2013 | Werneth et al. |
| 2013/0338467 A1 | 12/2013 | Grasse et al. |
| 2014/0005664 A1 | 1/2014 | Govari et al. |
| 2014/0024911 A1 | 1/2014 | Harlev et al. |
| 2014/0039288 A1 | 2/2014 | Shih |
| 2014/0051993 A1 | 2/2014 | McGee |
| 2014/0052118 A1 | 2/2014 | Laske et al. |
| 2014/0052126 A1 | 2/2014 | Long et al. |
| 2014/0052216 A1 | 2/2014 | Long et al. |
| 2014/0058377 A1 | 2/2014 | Deem et al. |
| 2014/0081113 A1 | 3/2014 | Cohen et al. |
| 2014/0100563 A1 | 4/2014 | Govari et al. |
| 2014/0107644 A1 | 4/2014 | Falwell et al. |
| 2014/0142408 A1 | 5/2014 | De La Rama et al. |
| 2014/0148804 A1 | 5/2014 | Ward et al. |
| 2014/0163480 A1 | 6/2014 | Govari et al. |
| 2014/0163546 A1 | 6/2014 | Govari et al. |
| 2014/0171942 A1 | 6/2014 | Werneth et al. |
| 2014/0180035 A1 | 6/2014 | Anderson |
| 2014/0187916 A1 | 7/2014 | Clark et al. |
| 2014/0194716 A1 | 7/2014 | Diep et al. |
| 2014/0194867 A1 | 7/2014 | Fish et al. |
| 2014/0200567 A1 | 7/2014 | Cox et al. |
| 2014/0235986 A1 | 8/2014 | Harlev et al. |
| 2014/0235988 A1 | 8/2014 | Ghosh |
| 2014/0235989 A1 | 8/2014 | Wodlinger et al. |
| 2014/0243851 A1 | 8/2014 | Cohen et al. |
| 2014/0276760 A1 | 9/2014 | Bonyak et al. |
| 2014/0276782 A1 | 9/2014 | Paskar |
| 2014/0276791 A1 | 9/2014 | Ku et al. |
| 2014/0288556 A1 | 9/2014 | Ibrahim et al. |
| 2014/0303721 A1 | 10/2014 | Fung et al. |
| 2014/0343549 A1 | 11/2014 | Spear et al. |
| 2014/0364845 A1 | 12/2014 | Rashidi |
| 2014/0371613 A1 | 12/2014 | Narayan et al. |
| 2015/0005767 A1 | 1/2015 | Werneth et al. |
| 2015/0011995 A1 | 1/2015 | Avitall et al. |
| 2015/0066108 A1 | 3/2015 | Shi et al. |
| 2015/0119674 A1 | 4/2015 | Fischell et al. |
| 2015/0126840 A1 | 5/2015 | Thakur et al. |
| 2015/0133914 A1 | 5/2015 | Koblish |
| 2015/0138977 A1 | 5/2015 | Dacosta |
| 2015/0141978 A1 | 5/2015 | Subramaniam et al. |
| 2015/0142041 A1 | 5/2015 | Kendale et al. |
| 2015/0148796 A1 | 5/2015 | Bencini |
| 2015/0150472 A1 | 6/2015 | Harlev et al. |
| 2015/0157402 A1 | 6/2015 | Kunis et al. |
| 2015/0157412 A1 | 6/2015 | Wallace et al. |
| 2015/0164584 A1 | 6/2015 | Davalos et al. |
| 2015/0173824 A1 | 6/2015 | Davalos et al. |
| 2015/0173828 A1 | 6/2015 | Avitall |
| 2015/0174404 A1 | 6/2015 | Rousso et al. |
| 2015/0182740 A1 | 7/2015 | Mickelsen |
| 2015/0196217 A1 | 7/2015 | Harlev et al. |
| 2015/0223726 A1 | 8/2015 | Harlev et al. |
| 2015/0230699 A1 | 8/2015 | Berul et al. |
| 2015/0258344 A1 | 9/2015 | Tandri et al. |
| 2015/0265342 A1 | 9/2015 | Long et al. |
| 2015/0265344 A1 | 9/2015 | Aktas et al. |
| 2015/0272656 A1 | 10/2015 | Chen |
| 2015/0272664 A9 | 10/2015 | Cohen |
| 2015/0272667 A1 | 10/2015 | Govari et al. |
| 2015/0282729 A1 | 10/2015 | Harlev et al. |
| 2015/0289923 A1 | 10/2015 | Davalos et al. |
| 2015/0304879 A1 | 10/2015 | Dacosta |
| 2015/0320481 A1 | 11/2015 | Cosman et al. |
| 2015/0321021 A1 | 11/2015 | Tandri et al. |
| 2015/0342532 A1 | 12/2015 | Basu et al. |
| 2015/0343212 A1 | 12/2015 | Rousso et al. |
| 2015/0351836 A1 | 12/2015 | Prutchi |
| 2015/0359583 A1 | 12/2015 | Swanson |
| 2016/0000500 A1 | 1/2016 | Salahieh et al. |
| 2016/0008061 A1 | 1/2016 | Fung et al. |
| 2016/0008065 A1 | 1/2016 | Gliner et al. |
| 2016/0029960 A1 | 2/2016 | Toth et al. |
| 2016/0038772 A1 | 2/2016 | Thapliyal et al. |
| 2016/0051204 A1 | 2/2016 | Harlev et al. |
| 2016/0051324 A1 | 2/2016 | Stewart et al. |
| 2016/0058493 A1 | 3/2016 | Neal, II et al. |
| 2016/0058506 A1 | 3/2016 | Spence et al. |
| 2016/0066993 A1 | 3/2016 | Avitall et al. |
| 2016/0074679 A1 | 3/2016 | Thapliyal et al. |
| 2016/0095531 A1 | 4/2016 | Narayan et al. |
| 2016/0095642 A1 | 4/2016 | Deno et al. |
| 2016/0095653 A1 | 4/2016 | Lambert et al. |
| 2016/0100797 A1 | 4/2016 | Mahapatra et al. |
| 2016/0100884 A1 | 4/2016 | Fay et al. |
| 2016/0106498 A1 | 4/2016 | Highsmith et al. |
| 2016/0106500 A1 | 4/2016 | Olson |
| 2016/0113709 A1 | 4/2016 | Maor |
| 2016/0113712 A1 | 4/2016 | Cheung et al. |
| 2016/0120564 A1 | 5/2016 | Kirkpatrick et al. |
| 2016/0128770 A1 | 5/2016 | Afonso et al. |
| 2016/0166167 A1 | 6/2016 | Narayan et al. |
| 2016/0166310 A1 | 6/2016 | Stewart et al. |
| 2016/0166311 A1 | 6/2016 | Long et al. |
| 2016/0174865 A1 | 6/2016 | Stewart et al. |
| 2016/0184003 A1 | 6/2016 | Srimathveeravalli et al. |
| 2016/0184004 A1 | 6/2016 | Hull et al. |
| 2016/0213282 A1 | 7/2016 | Leo et al. |
| 2016/0220307 A1 | 8/2016 | Miller et al. |
| 2016/0235470 A1 | 8/2016 | Callas et al. |
| 2016/0287314 A1 | 10/2016 | Arena et al. |
| 2016/0310211 A1 | 10/2016 | Long |
| 2016/0324564 A1 | 11/2016 | Gerlach et al. |
| 2016/0324573 A1 | 11/2016 | Mickelsen et al. |
| 2016/0331441 A1 | 11/2016 | Konings |
| 2016/0331459 A1 | 11/2016 | Townley et al. |
| 2016/0354142 A1 | 12/2016 | Pearson et al. |
| 2016/0361109 A1 | 12/2016 | Weaver et al. |
| 2017/0001016 A1 | 1/2017 | De Ridder |
| 2017/0035499 A1 | 2/2017 | Stewart et al. |
| 2017/0042449 A1 | 2/2017 | Deno et al. |
| 2017/0042615 A1 | 2/2017 | Salahieh et al. |
| 2017/0056648 A1 | 3/2017 | Syed et al. |
| 2017/0065330 A1 | 3/2017 | Mickelsen et al. |
| 2017/0065339 A1 | 3/2017 | Mickelsen |
| 2017/0065340 A1 | 3/2017 | Long |
| 2017/0065343 A1 | 3/2017 | Mickelsen |
| 2017/0071543 A1 | 3/2017 | Basu et al. |
| 2017/0095291 A1 | 4/2017 | Harrington et al. |
| 2017/0105793 A1 | 4/2017 | Cao et al. |
| 2017/0146584 A1 | 5/2017 | Daw et al. |
| 2017/0151029 A1 | 6/2017 | Mickelsen |
| 2017/0172654 A1 | 6/2017 | Wittkampf et al. |
| 2017/0181795 A1 | 6/2017 | Debruyne |
| 2017/0189097 A1 | 7/2017 | Viswanathan et al. |
| 2017/0215953 A1 | 8/2017 | Long et al. |
| 2017/0245928 A1 | 8/2017 | Xiao et al. |
| 2017/0246455 A1 | 8/2017 | Athos et al. |
| 2017/0312024 A1 | 11/2017 | Harlev et al. |
| 2017/0312025 A1 | 11/2017 | Harlev et al. |
| 2017/0312027 A1 | 11/2017 | Harlev et al. |
| 2018/0001056 A1 | 1/2018 | Leeflang et al. |
| 2018/0042674 A1 | 2/2018 | Mickelsen |
| 2018/0042675 A1 | 2/2018 | Long |
| 2018/0043153 A1 | 2/2018 | Viswanathan et al. |
| 2018/0064488 A1 | 3/2018 | Long et al. |
| 2018/0085160 A1 | 3/2018 | Viswanathan et al. |
| 2018/0093088 A1 | 4/2018 | Mickelsen |
| 2018/0168511 A1 | 6/2018 | Hall et al. |
| 2018/0200497 A1 | 7/2018 | Mickelsen |
| 2018/0303488 A1 | 10/2018 | Hill |
| 2018/0311497 A1 | 11/2018 | Viswanathan et al. |

(56) References Cited

U.S. PATENT DOCUMENTS

| | | |
|---|---|---|
| 2018/0360534 A1 | 12/2018 | Teplitsky et al. |
| 2019/0069950 A1 | 3/2019 | Viswanathan et al. |
| 2019/0151015 A1 | 5/2019 | Viswanathan et al. |
| 2019/0231421 A1 | 8/2019 | Viswanathan et al. |
| 2019/0269912 A1 | 9/2019 | Viswanathan et al. |
| 2019/0336198 A1 | 11/2019 | Viswanathan et al. |
| 2019/0336207 A1 | 11/2019 | Viswanathan |

FOREIGN PATENT DOCUMENTS

| | | |
|---|---|---|
| EP | 0797956 | 6/2003 |
| EP | 1127552 | 6/2006 |
| EP | 1340469 | 3/2007 |
| EP | 1009303 | 6/2009 |
| EP | 2213729 | 8/2010 |
| EP | 2425871 | 3/2012 |
| EP | 1803411 | 8/2012 |
| EP | 2532320 A2 | 12/2012 |
| EP | 2587275 | 5/2013 |
| EP | 2663227 | 11/2013 |
| EP | 1909678 | 1/2014 |
| EP | 2217165 | 3/2014 |
| EP | 2376193 | 3/2014 |
| EP | 2708181 | 3/2014 |
| EP | 2777579 A1 | 9/2014 |
| EP | 2934307 | 10/2015 |
| EP | 2777585 | 6/2016 |
| EP | 2382935 B1 | 3/2018 |
| EP | 3111871 B1 | 3/2018 |
| EP | 3151773 B1 | 4/2018 |
| JP | H06-507797 | 9/1994 |
| JP | H10-510745 | 10/1998 |
| JP | 2000-508196 | 7/2000 |
| JP | 2005-516666 | 6/2005 |
| JP | 2006-506184 | 2/2006 |
| JP | 2007-325935 | 12/2007 |
| JP | 2008-538997 | 11/2008 |
| JP | 2009-500129 | 1/2009 |
| JP | 2011-509158 | 3/2011 |
| JP | 2012-050538 | 3/2012 |
| WO | WO 92/07622 | 5/1992 |
| WO | WO 92/21278 | 12/1992 |
| WO | WO 92/21285 | 12/1992 |
| WO | WO 94/07413 | 4/1994 |
| WO | WO 97/24073 | 7/1997 |
| WO | WO 97/25917 | 7/1997 |
| WO | WO 97/37719 | 10/1997 |
| WO | WO 1999/004851 | 2/1999 |
| WO | WO 1999/022659 | 5/1999 |
| WO | WO 1999/056650 | 11/1999 |
| WO | WO 1999/059486 | 11/1999 |
| WO | WO 2002/056782 | 7/2002 |
| WO | WO 2003/053289 | 7/2003 |
| WO | WO 2003/065916 | 8/2003 |
| WO | WO 2004/045442 | 6/2004 |
| WO | WO 2004/086994 | 10/2004 |
| WO | WO 2005/046487 | 5/2005 |
| WO | WO 2006/115902 | 11/2006 |
| WO | WO 2007/006055 | 1/2007 |
| WO | WO 2007/079438 | 7/2007 |
| WO | WO 2009/082710 | 7/2009 |
| WO | WO 2009/089343 | 7/2009 |
| WO | WO 2009/137800 | 11/2009 |
| WO | WO 2010/014480 | 2/2010 |
| WO | WO 2011/028310 | 3/2011 |
| WO | WO 2011/154805 | 12/2011 |
| WO | WO 2012/051433 | 4/2012 |
| WO | WO 2012/153928 | 11/2012 |
| WO | WO 2013/019385 | 2/2013 |
| WO | WO 2014/025394 | 2/2014 |
| WO | WO 2014/031800 | 2/2014 |
| WO | WO 2014/160832 | 10/2014 |
| WO | WO 2015/066322 | 5/2015 |
| WO | WO 2015/099786 | 7/2015 |
| WO | WO 2015/103530 | 7/2015 |
| WO | WO 2015/103574 | 7/2015 |
| WO | WO 2015/130824 | 9/2015 |
| WO | WO 2015/143327 | 9/2015 |
| WO | WO 2015/171921 | 11/2015 |
| WO | WO 2015/175944 | 11/2015 |
| WO | WO 2015/192018 | 12/2015 |
| WO | WO 2015/192027 | 12/2015 |
| WO | WO 2016/059027 | 4/2016 |
| WO | WO 2016/060983 | 4/2016 |
| WO | WO 2016/081650 | 5/2016 |
| WO | WO 2016/090175 | 6/2016 |
| WO | WO 2017/119934 | 7/2017 |
| WO | WO 2017/120169 | 7/2017 |
| WO | WO 2017/192477 | 11/2017 |
| WO | WO 2017/192495 | 11/2017 |
| WO | WO 2017/218734 | 12/2017 |
| WO | WO 2018/200800 | 11/2018 |

OTHER PUBLICATIONS

Supplementary European Search Report for European Application No. 13827672.0, dated Jul. 11, 2016, 12 pages.
Office Action for European Application No. 13827672.0, dated Feb. 5, 2018, 6 pages.
Notice of Reasons for Rejection for Japanese Application No. 2015-526522, dated Mar. 6, 2017, 3 pages.
Office Action for U.S. Appl. No. 14/400,455, dated Mar. 30, 2017, 10 pages.
International Search Report and Written Opinion for International Application No. PCT/US2013/031252, dated Jul. 19, 2013, 12 pages.
Office Action for U.S. Appl. No. 15/819,726, dated Jun. 4, 2018, 17 pages.
Office Action for U.S. Appl. No. 15/917,194, dated Jun. 4, 2018, 17 pages.
Office Action for U.S. Appl. No. 15/917,194, dated Oct. 9, 2018, 13 pages.
First Office Action for Chinese Application No. 201580006848.8, dated Jan. 29, 2018, 15 pages.
Office Action for U.S. Appl. No. 15/201,997, dated Dec. 17, 2018, 17 pages.
International Search Report and Written Opinion for International Application No. PCT/US2018/050660, dated Nov. 26, 2018, 13 pages.
Office Action for European Application No. 15701856.5, dated Dec. 11, 2017, 6 pages.
Notice of Reasons for Rejection for Japanese Application No. 2016-544072, dated Oct. 1, 2018, 11 pages.
International Search Report and Written Opinion for International Application No. PCT/US2015/010138, dated Mar. 26, 2015, 14 pages.
International Preliminary Report on Patentability for International Application No. PCT/US2015/010138, dated Jul. 12, 2016, 9 pages.
Supplementary European Search Report for European Application No. 15733297.4, dated Aug. 10, 2017, 7 pages.
Office Action for U.S. Appl. No. 15/201,997, dated Apr. 3, 2017, 6 pages.
Office Action for U.S. Appl. No. 15/201,997, dated Aug. 29, 2017, 12 pages.
Office Action for U.S. Appl. No. 15/201,997, dated Jul. 12, 2018, 12 pages.
International Search Report and Written Opinion for International Application No. PCT/US2015/010223, dated Apr. 10, 2015, 19 pages.
International Preliminary Report on Patentability for International Application No. PCT/US2015/010223, dated Jul. 12, 2016, 12 pages.
International Search Report and Written Opinion for International Application No. PCT/US2015/029734, dated Nov. 24, 2015, 15 pages.
Office Action for U.S. Appl. No. 15/795,062, dated Dec. 19, 2017, 14 pages.

(56) References Cited

OTHER PUBLICATIONS

Office Action for U.S. Appl. No. 15/795,062, dated Apr. 9, 2018, 20 pages.
International Search Report and Written Opinion for International Application No. PCT/US2015/031086, dated Oct. 21, 2015, 16 pages.
Office Action for U.S. Appl. No. 15/795,075, dated Feb. 6, 2018, 9 pages.
Office Action for U.S. Appl. No. 15/795,075, dated Jun. 15, 2018, 10 pages.
Extended European Search Report for European Application No. 15849844.4, dated May 3, 2018, 8 pages.
International Search Report and Written Opinion for International Application No. PCT/US2015/055105, dated Mar. 1, 2016, 15 pages.
Office Action for U.S. Appl. No. 15/796,255, dated Jan. 10, 2018, 12 pages.
Extended European Search Report for European Application No. 15806855.1, dated Jan. 3, 2018, 8 pages.
International Search Report and Written Opinion for International Application No. PCT/US2015/035582, dated Oct. 2, 2015, 17 pages.
Extended European Search Report for European Application No. 15806278.6, dated Feb. 9, 2018, 5 pages.
International Search Report and Written Opinion for International Application No. PCT/US2015/035592, dated Oct. 2, 2015, 13 pages.
Office Action for U.S. Appl. No. 15/334,646, dated Jul. 25, 2017, 19 pages.
Office Action for U.S. Appl. No. 15/334,646, dated Nov. 16, 2017, 26 pages.
International Search Report and Written Opinion for International Application No. PCT/US2016/057664, dated Feb. 24, 2017, 11 pages.
Office Action for U.S. Appl. No. 15/796,375, dated Jan. 24, 2018, 25 pages.
Office Action for U.S. Appl. No. 15/796,375, dated May 30, 2018, 26 pages.
Office Action for U.S. Appl. No. 15/796,375, dated Nov. 16, 2018, 27 pages.
International Search Report and Written Opinion for International Application No. PCT/US2017/012099, dated May 18, 2017, 17 pages.
Office Action for U.S. Appl. No. 15/711,266, dated Feb. 23, 2018, 14 pages.
International Search Report and Written Opinion for International Application No. PCT/US2018/029938, dated Aug. 29, 2018, 14 pages.
International Search Report and Written Opinion for International Application No. PCT/US2017/037609, dated Nov. 8, 2017, 13 pages.
Office Action for U.S. Appl. No. 15/672,916, dated Feb. 13, 2018, 16 pages.
Office Action for U.S. Appl. No. 15/672,916, dated Jul. 20, 2018, 23 pages.
Office Action for U.S. Appl. No. 15/499,804, dated Jan. 3, 2018, 20 pages.
Office Action for U.S. Appl. No. 15/794,717, dated Feb. 1, 2018, 10 pages.
International Search Report and Written Opinion for International Application No. PCT/US2018/029552, dated Jun. 29, 2018, 13 pages.
Office Action for U.S. Appl. No. 15/970,404, dated Oct. 9, 2018, 21 pages.
du Pre, B.C. et al., "Minimal coronary artery damage by myocardial electroporation ablation," Europace, 15(1):144-149 (2013).
Hobbs, E. P., "Investor Relations Update: Tissue Ablation via Irreversible Electroporation (IRE)," Powerpoint (2004), 16 pages.
Lavee, J. et al., "A Novel Nonthermal Energy Source for Surgical Epicardial Atrial Ablation: Irreversible Electroporation," The Heart Surgery Forum #2006-1202, 10(2), 2007 [Epub Mar. 2007].
Madhavan, M. et al., "Novel Percutaneous Epicardial Autonomic Modulation in the Canine for Atrial Fibrillation: Results of an Efficacy and Safety Study," Pace, 00:1-11 (2016).
Neven, K. et al., "Safety and Feasibility of Closed Chest Epicardial Catheter Ablation Using Electroporation," Circ Arrhythm Electrophysiol., 7:913-919 (2014).
Neven, K. et al., "Myocardial Lesion Size After Epicardial Electroporation Catheter Ablation After Subxiphoid Puncture," Circ Arrhythm Electrophysiol., 7(4):728-733 (2014).
Neven, K. et al., "Epicardial linear electroporation ablation and lesion size," Heart Rhythm, 11:1465-1470 (2014).
van Driel, V.J.H.M. et al., "Pulmonary Vein Stenosis After Catheter Ablation Electroporation Versus Radiofrequency," Circ Arrhythm Electrophysiol., 7(4):734-738 (2014).
van Driel, V.J.H.M. et al., "Low vulnerability of the right phrenic nerve to electroporation ablation," Heart Rhythm, 12:1838-1844 (2015).
Wittkampf, F.H. et al., "Myocardial Lesion Depth With Circular Electroporation Ablation," Circ. Arrhythm Electrophysiol., 5(3):581-586 (2012).
Wittkampf, F.H. et al., "Feasibility of Electroporation for the Creation of Pulmonary Vein Ostial Lesions," J Cardiovasc Electrophysiol, 22(3):302-309 (Mar. 2011).
Office Action for Canadian Application No. 2,881,462, dated Mar. 19, 2019, 5 pages.
Office Action for Japanese Application No. 2018-036714, dated Jan. 16, 2019, 8 pages.
Office Action for U.S. Appl. No. 15/201,983, dated Apr. 3, 2019, 16 pages.
Office Action for U.S. Appl. No. 15/341,523, dated Jan. 29, 2019, 10 pages.
Office Action for U.S. Appl. No. 15/795,075, dated Apr. 10, 2019, 11 pages.
Office Action for U.S. Appl. No. 15/672,916, dated Apr. 9, 2019, 31 pages.
Partial European Search Report for European Application No. 18170210.1, dated Feb. 14, 2019, 13 pages.
Office Action for U.S. Appl. No. 15/970,404, dated Apr. 12, 2019, 20 pages.
Office Action for U.S. Appl. No. 15/917,194, dated Apr. 29, 2019, 10 pages.
Office Action for U.S. Appl. No. 15/795,062, dated May 3, 2019, 21 pages.
International Search Report and Written Opinion for International Application No. PCT/US2019/014226, dated Apr. 29, 2019, 15 pages.
Extended European Search Report for European Application No. 18189811.5, dated May 14, 2019, 7 pages.
International Search Report and Written Opinion for International Application No. PCT/US2019/017322, dated May 10, 2019, 15 pages.
Office Action for U.S. Appl. No. 15/341,512, dated Aug. 1, 2019, 19 pages.
Office Action for U.S. Appl. No. 15/341,523, dated Jul. 30, 2019, 8 pages.
Office Action for U.S. Appl. No. 15/795,075, dated Jul. 31, 2019, 12 pages.
Office Action for U.S. Appl. No. 15/484,969, dated Sep. 4, 2019, 12 pages.
Office Action for U.S. Appl. No. 15/354,475, dated May 23, 2019, 7 pages.
Extended European Search Report for European Application No. 16884132.8, dated Jul. 8, 2019, 7 pages.
Office Action for U.S. Appl. No. 16/416,677, dated Aug. 15, 2019, 8 pages.
Extended European Search Report for European Application No. 17736218.3 dated Aug. 23, 2019, 9 pages.
Office Action for U.S. Appl. No. 16/181,027, dated Sep. 4, 2019, 12 pages.

(56) References Cited

OTHER PUBLICATIONS

Office Action for U.S. Appl. No. 16/240,066, dated May 29, 2019, 7 pages.
Extended European Search Report for European Application No. 18170210.1, dated May 17, 2019, 11 pages.
International Search Report and Written Opinion for International Application No. PCT/US2019/030922, dated Sep. 6, 2019, 12 pages.
International Search Report and Written Opinion for International Application No. PCT/US2019/030882, dated Sep. 10, 2019, 17 pages.
Office Action for U.S. Appl. No. 16/405,515, dated Sep. 6, 2019, 9 pages.
International Search Report and Written Opinion for International Application No. PCT/US2019/031135, dated Aug. 5, 2019, 11 pages.
International Search Report and Written Opinion for International Application No. PCT/US2019/028943, dated Sep. 17, 2019, 17 pages.
Extended European Search Report for European Application No. 19182099.2, dated Dec. 13, 2019, 7 pages.
Office Action for U.S. Appl. No. 15/917,194, dated Dec. 20, 2019, 10 pages.
Office Action for U.S. Appl. No. 15/201,983, dated Nov. 15, 2019, 15 pages.
Office Action for U.S. Appl. No. 15/341,512, dated Nov. 12, 2019, 18 pages.
Office Action for U.S. Appl. No. 15/795,062, dated Nov. 4, 2019, 23 pages.
Office Action for U.S. Appl. No. 16/375,561, dated Oct. 17, 2019, 15 pages.
Office Action for U.S. Appl. No. 15/970,404, dated Nov. 12, 2019, 19 pages.
Office Action for Japanese Application No. 2018-036714, dated Nov. 27, 2019, 5 pages.
Office Action for U.S. Appl. No. 16/741,506, dated Feb. 28, 2020, 5 pages.

* cited by examiner

SYSTEMS, APPARATUSES, AND METHODS FOR DETECTING ECTOPIC ELECTROCARDIOGRAM SIGNALS DURING PULSED ELECTRIC FIELD ABLATION

BACKGROUND

Application of brief ultra-short high voltage pulses to tissue may generate high electric fields in tissue to generate a local region of ablated tissue by the biophysical mechanism of irreversible electroporation.

In cardiac applications, high voltage pulses, however, may cause complications such as induced arrhythmias (e.g., ventricular fibrillation) if delivered during certain periods of cardiac activity. Accordingly, it can be desirable to delivery high voltage pulses for pulsed electric field ablation in synchrony with the cardiac cycle so as to avoid the risk of such complications,

DETAILED DESCRIPTION

Figure 1:
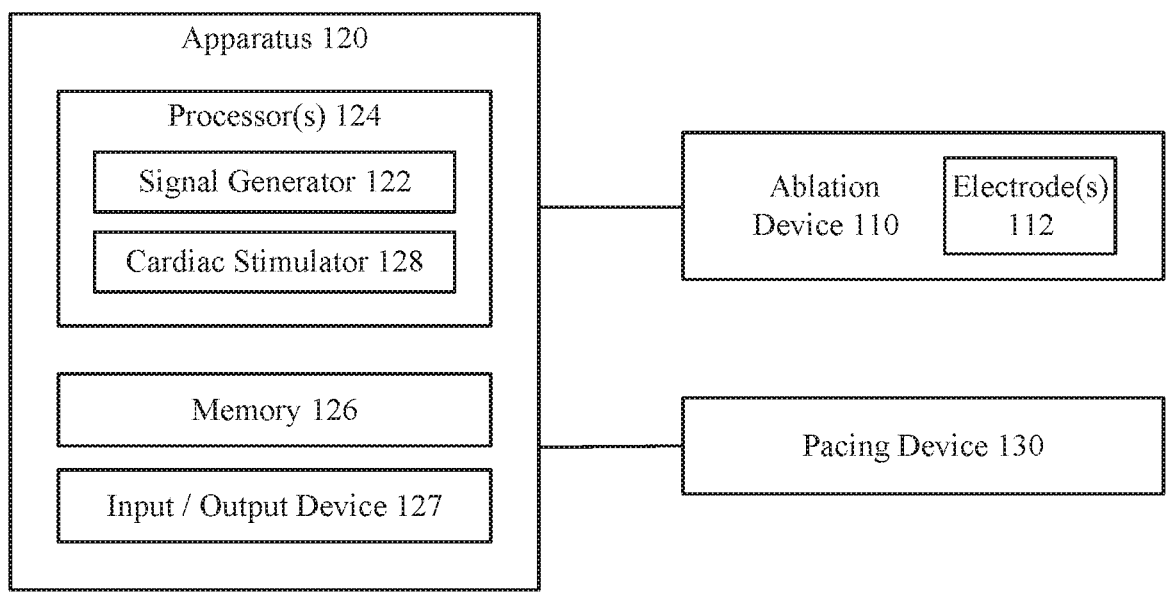
FIG. 1 is a block diagram of a system, according to embodiments.

Described herein are systems, devices, and methods for detecting ectopic cardiac activity in connection with delivery of ablation energy to tissue such as pulsed electric field ablation. Pulsed electric field ablation uses ultra-short high-voltage pulses to generate large electric fields at desired regions of interest to generate a local region of ablated tissue via irreversible electroporation. In certain applications, including cardiac applications, it can be desirable to generate pulses for pulsed electric field ablation in synchronicity with a cardiac cycle. Synchronizing ablation energy delivery with the cardiac cycle may reduce the risk of induced arrhythmias such as atrial and/or ventricular fibrillation. One method of synchronizing delivery of pulses can be to pace of stimulate one or more cardiac cambers with periodic pacing signals with a predefined time period. For example, a cardiac stimulator may be used to deliver pacing pulses to one or more cardiac chambers such that the cardiac rhythm of a patient synchronizes with the pacing pulse. In some embodiments, pacing pulses can be delivered to the cardiac chamber(s) via an intracardiac catheter that is suitably positioned in the chamber(s). The intracardiac catheter can include one or more electrodes that are used to conduct the pacing signal into the heart. For example, the catheter can have a pair of electrodes (e.g., a most distal electrode and an electrode proximal to the distal electrode) that is used as a bipolar pair to deliver a pacing signal, with the two electrodes providing the forward and return current paths for the pacing signal. The pacing pulse can cause the cardiac chamber to generate its electrocardiogram (ECG) pulses in synchrony with the pacing pulses, thereby controlling the timing of the cardiac cycle.

Once the periodicity of the cardiac cycle is established and confirmed, e.g., by a physician, the delivery of high voltage ablation pulses can be timed to start in synchrony with the pacing signals. For example, the ablation pulses can be delivered with predetermined offsets from the pacing signals such that their delivery falls within the refractory window following the QRS waveform of the cardiac cycle. In some embodiments, the ablation pulses can be delivered to a cardiac chamber using an ablation catheter configured for pulsed electric field ablation.

While a cardiac chamber is being paced, however, localized electrical activity (e.g., pre-ventricular contraction (PVC)) may trigger ectopic cardiac activity that generates an additional localized T-wave (e.g., ectopic beat) that may overlap the next pacing pulse. Ablation energy delivered during these localized T-waves may have a high risk of inducing fibrillation.

Accordingly, it can be desirable to detect such localized or ectopic ECG activity that can occur between successive pacing pulses during ablation, such that the ablation system can ensure that ablation is not delivered during those times. For example, an ablation device can be configured to be disconnected from a signal generator when ectopic activity has been detected. By disconnecting or switching off the ablation device (for example, with a suitable relay), the risk of inducing a fibrillation event can be reduced.

Systems, devices, and methods described herein can be configured to detect ectopic signals and to control the operation of an ablation device based on such detection. For example, a system as described herein may include a cardiac stimulator and pacing device used to electrically pace the heart and ensure pacing capture to establish periodicity and predictability of the cardiac cycle. The pacing device may be configured to measure electrical cardiac activity (e.g., an electrocardiogram (ECG) signal) used to confirm pacing capture and/or detect ectopic cardiac activity. For example, predetermined portions of an ECG signal may be analyzed for an ectopic beat and synchronization between a pacing pulse and cardiac cycle. A cardiac activity status may be output to indicate the status of pacing capture and/or ectopic cardiac activity, and be used to control delivery of ablation energy to tissue.

The system may further include a signal generator and a processor configured to apply one or more voltage pulse waveforms to a selected set of electrodes of an ablation device to deliver energy to a region of interest (e.g., ablation energy for a set of tissue in a pulmonary vein ostium). The pulse waveforms disclosed herein may aid in therapeutic treatment of a variety of cardiac arrhythmias (e.g., atrial fibrillation).

The cardiac stimulator may synchronize the generation of the pulse waveform to a paced heartbeat in order to reduce unintended tissue damage. For example, a time window within a refractory period of the periodic cardiac cycle may be selected for voltage pulse waveform delivery. Thus, voltage pulse waveforms may be delivered in the refractory period of the cardiac cycle so as to avoid disruption of the sinus rhythm of the heart. The pulse waveform may be generated based on a cardiac activity status indicating an absence of an ectopic beat and confirmation of pacing capture. For example, the pulse waveform may be generated in synchronization with a pacing signal of the heart to avoid disruption of the sinus rhythm of the heart, and can be delivered outside of periods of detected ectopic activity. The pulse waveform can be delivered to one or more electrodes of one or more catheters that are epicardially or endocardially placed around the heart, such that those electrodes generate a pulsed electric field to ablate tissue. In some embodiments, the pulse waveform may include hierarchical waveforms to aid in tissue ablation and reduce damage to healthy tissue.

In some embodiments, an apparatus includes a memory and a processor operatively coupled to the memory. The processor can be configured to receive cardiac signal data captured by a set of electrodes; extract a sliding window of the cardiac signal data; identify a peak frequency over a subrange of frequencies associated with the extracted sliding window; detect ectopic activity based at least on a measure of the peak frequency over the subrange of frequencies; and in response to detecting ectopic activity, send an indication of ectopic activity to a signal generator configured to generate pulsed waveforms for cardiac ablation such that the signal generator is deactivated or switched off from generating the pulsed waveforms.

In some embodiments, an apparatus includes a memory and a processor operatively coupled to the memory. The processor can be configured to receive cardiac signal data captured by a set of electrodes; receive an indication of delivery of a set of pacing pulses to the cardiac tissue; extract portions of the cardiac signal data following delivery of a subset of successive pacing pulses from the set of pacing pulses; calculate, for each extracted portion, a set of moments of a function associated with that extracted portion; confirm pacing capture of the set of pacing pulses based at least on the set of moments calculated for each extracted portion; and in response to confirming pacing capture, send an indication of pacing capture to a signal generator configured to generate pulsed waveforms for cardiac ablation such that the signal generator is activated for generating the pulsed waveforms. In some embodiments, the processor is further configured to: analyze local peak frequencies of the cardiac signal data to detect ectopic activity; and in response to detecting ectopic activity, send an indication of ectopic activity to the signal generator such that the signal generator is switched off from generating the pulsed waveforms.

In some embodiments, a system includes a first controller configured to generate a pulsed waveform and deliver the pulsed waveform in synchrony with a set of pacing pulses to an ablation device; and a second controller operatively coupled to the first controller, the second controller configured to: generate the set of pacing pulses and deliver the set of pacing pulses to a pacing device; receive cardiac signal data captured by a set of electrodes; confirm pacing capture of the set of pacing pulses based on the cardiac signal data; and in response to confirming pacing capture, send an indication of pacing capture to the first controller to activate generation of the pulsed waveform. In some embodiments, the second controller is further configured to: monitor the cardiac signal data for ectopic activity; and when ectopic activity is present, send an indication of ectopic activity to the first controller to switch off generation of the pulsed waveform.

In some embodiments, a method includes receiving cardiac signal data captured by a set of electrodes disposed near cardiac tissue; extracting a sliding window of the cardiac signal data; identifying a peak frequency over a subrange of frequencies associated with the extracted sliding window; detecting ectopic activity based at least on a measure of the peak frequency over the subrange of frequencies; and in response to detecting ectopic activity, sending an indication of ectopic activity to a signal generator configured to generate pulsed waveforms for cardiac ablation such that the signal generator is switch off from generating the pulsed waveforms. The method can further include confirming pacing capture of the set of pacing pulses based on the cardiac signal data.

The term "electroporation" as used herein refers to the application of an electric field to a cell membrane to change the permeability of the cell membrane to the extracellular environment. The term "reversible electroporation" as used herein refers to the application of an electric field to a cell membrane to temporarily change the permeability of the cell membrane to the extracellular environment. For example, a cell undergoing reversible electroporation can observe the temporary and/or intermittent formation of one or more pores in its cell membrane that close up upon removal of the electric field. The term "irreversible electroporation" as used herein refers to the application of an electric field to a cell membrane to permanently change the permeability of the cell membrane to the extracellular environment. For example, a cell undergoing irreversible electroporation can observe the formation of one or more pores in its cell membrane that persist upon removal of the electric field.

Pulse waveforms for electroporation energy delivery as disclosed herein may enhance the safety, efficiency and effectiveness of energy delivery to tissue by reducing the electric field threshold associated with irreversible electroporation, thus yielding more effective ablative lesions with a reduction in total energy delivered. In some embodiments, the voltage pulse waveforms disclosed herein may be hierarchical and have a nested structure. For example, the pulse waveform may include hierarchical groupings of pulses having associated timescales. In some embodiments, the methods, systems, and devices disclosed herein may comprise one or more of the methods, systems, and devices described in International Application Serial No. PCT/US2019/014226, filed on Jan. 18, 2019, published as International Publication No. WO/2019/143960 on Jul. 25, 2019, and titled "SYSTEMS, DEVICES AND METHODS FOR FOCAL ABLATION," the contents of which are hereby incorporated by reference in its entirety.

Systems

Disclosed herein are systems and devices configured for monitoring ectopic cardiac activity in connection with tissue ablation via the selective and rapid application of voltage pulse waveforms resulting in irreversible electroporation. Generally, a system for ablating tissue described here may include a cardiac stimulator for generating a pacing signal delivered by a pacing device to the heart. The system further measures electrical cardiac activity for identification of ectopic beats and/or to confirm pacing capture of the heart. The detected pacing signal and/or detected cardiac activity can be used to control delivery of a pulse waveform generated by a signal generator to an ablation device having one or more electrodes. As described herein, the systems and devices may be deployed epicardially and/or endocardially to treat heart conditions such as, for example, atrial fibrillation. Voltages may be applied to a selected subset of the electrodes, with independent subset selections for anode and cathode electrode selections.

Generally, the systems and devices described herein include one or more devices (e.g., catheters) configured to ablate tissue in a left atrial chamber of a heart. FIG. 1 illustrates a system (100) configured to deliver voltage pulse waveforms. The system (100) may include an apparatus (120) including one or more processor(s) or controller(s) (124) and a memory (126). The processor(s) (124) can function as, be integrated into, and/or control a signal generator (122) and/or a cardiac stimulator (128).

Each of the one or more processor(s) (124) may be any suitable processing device configured to run and/or execute a set of instructions or code. The processor may be, for example, a general purpose processor, a Field Programmable Gate Array (FPGA), an Application Specific Integrated Circuit (ASIC), a Digital Signal Processor (DSP), and/or the like. The processor may be configured to run and/or execute application processes and/or other modules, processes and/or functions associated with the system and/or a network associated therewith (not shown). The underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, and/or the like.

The memory (126) may include a database (not shown) and may be, for example, a random access memory (RAM), a memory buffer, a hard drive, an erasable programmable read-only memory (EPROM), an electrically erasable read-only memory (EEPROM), a read-only memory (ROM), Flash memory, etc. The memory (126) may store instructions to cause the processor (124) to execute modules, processes and/or functions associated with the system (100), such as pulse waveform generation and/or cardiac pacing.

The apparatus (120) may be coupled to an ablation device (110) and/or a pacing device (130). When coupled to the ablation device (110) and pacing device (130), one or more components of the apparatus (120) (e.g., a processor (124) functioning as a signal generator (122) and/or cardiac stimulator (128)) can be in electrical communication with the ablation device (110) and/or pacing device (130) to control delivery of pacing signals, ablation signals, etc. via the ablation device (110) and pacing device (130) and/or to receive data (e.g., sensed signals) from the ablation device (110) and pacing device (130). If apparatus (120) includes multiple processors (124), one or more of the processor(s) (124) can communicate with one another to control pacing and/or ablation. The apparatus (120) can also include an input/output device (127) that enables the apparatus (120) to interface with other devices (e.g., ablation device (110) and/or pacing device (130)) and/or a user. For example, the apparatus (120) can include a user interface, e.g., a display, an audio device, etc. that enables presentation of outputs to a user and/or receipt of input from the user.

The signal generator (122) may be configured to generate ablation pulse waveforms for irreversible electroporation of tissue, such as, for example, pulmonary vein ostia. For example, the signal generator (122) may be a voltage pulse waveform generator and deliver a pulse waveform to the ablation device (110). The processor (124) may incorporate data received from memory (126), cardiac stimulator (128), and pacing device (130) to determine the parameters (e.g., timing, amplitude, width, duty cycle, etc.) of the pulse waveform to be generated by the signal generator (122). The memory (126) may further store instructions to cause the signal generator (122) to execute modules, processes and/or functions associated with the system (100), such as ectopic cardiac activity detection, pulse waveform generation, and/or cardiac pacing synchronization. For example, the memory (126) may be configured to store one or more of cardiac activity data, pulse waveform, and heart pacing data.

The pacing device (130) disposed in the patient may be configured to receive a heart pacing signal generated by the cardiac stimulator (128) of the apparatus (120) for cardiac stimulation. An indication of the pacing signal may be transmitted by the cardiac stimulator (128) to the signal generator (122). Based on the pacing signal, an indication of a voltage pulse waveform may be selected, computed, and/or otherwise identified by the processor (124) and generated by the signal generator (122). In some embodiments, the signal generator (122) is configured to generate the pulse waveform based on a cardiac activity status where the pulse waveform is in synchronization with the indication of the pacing signal (e.g., within a common refractory window). For example, in some embodiments, the common refractory window may start substantially immediately following a ventricular pacing signal (or after a very small delay) and last for a duration of approximately 250 milliseconds (ms) or less thereafter. In such embodiments, an entire pulse waveform may be delivered within this duration.

In some embodiments, one or more intracardiac electrodes, e.g., of the pacing device (130) and/or ablation device (110), can be configured to sense signals within the heart and deliver those signals to one or more of the processor(s) 124. The one or more processor(s) 124 can analyze the sensed signals for ectopic activity and control operation of the signal generator (122) based on such analysis, as further described below.

The system (100) may be in communication with other devices (not shown) via, for example, one or more networks, each of which may be any type of network. A wireless network may refer to any type of digital network that is not connected by cables of any kind. However, a wireless network may connect to a wireline network in order to interface with the Internet, other carrier voice and data networks, business networks, and personal networks. A wireline network is typically carried over copper twisted pair, coaxial cable or fiber optic cables. There are many different types of wireline networks including, wide area networks (WAN), metropolitan area networks (MAN), local area networks (LAN), campus area networks (CAN), global area networks (GAN), like the Internet, and virtual private networks (VPN). Hereinafter, network refers to any combination of combined wireless, wireline, public and private data networks that are typically interconnected through the Internet, to provide a unified networking and information access solution. The system (100) may further comprise one or more output devices such as a display, audio device, touchscreen, combinations thereof, and the like.

Figure 2:
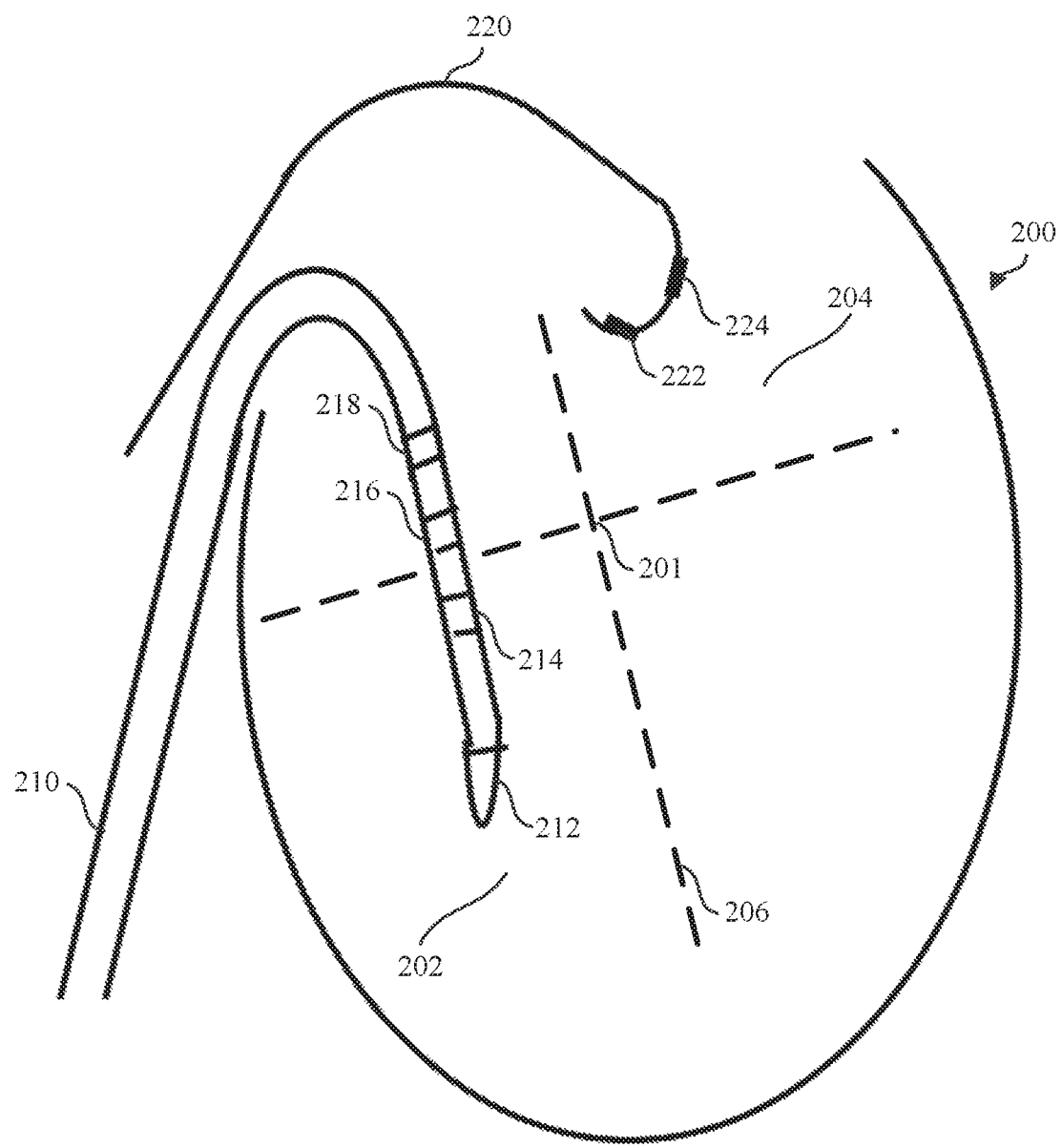
FIG. 2 is a schematic cross-sectional illustration of an ablation catheter and a pacing catheter disposed in a heart, according to embodiments.

FIG. 2 is a schematic illustration of a heart (200), e.g., as seen from an anterior side (e.g., front of a subject) including an ablation device (220) and a pacing device (210) disposed therein, according to embodiments described herein. The pacing device (210) may be configured to measure cardiac activity and/or deliver pacing signal to the heart (200), and the ablation device (220) may be configured to receive and/or deliver a pulse waveform to cardiac tissue. As illustrated, in the anterior cross-section of the heart (200)

depicted in FIG. 2, the dotted lines (201) schematically approximate the boundaries of the four heart chambers including the right ventricle RV (202) and left atrium LA (204). Pacing device (210) may be introduced into the right ventricle (202) and positioned such that it can stimulate the right ventricle (202) and obtain pacing capture. The pacing device (210) may comprise first electrode (212), second electrode (214), third electrode (216), and fourth electrode (218). The first electrode (212) and the second electrode (214) may be configured as a bipolar pair of pacing electrodes to pace the right ventricle (202). The pacing electrodes (212, 214) may be coupled to a cardiac stimulator (e.g., cardiac stimulator (128)). The third electrode (216) and the fourth electrode (218) may be configured as sensor elements to measure intracardiac activity (e.g., ECG signal) of the heart (200). While the pacing device (210) is described as being positioned in the right ventricle (202), it can be appreciated that the pacing device (210) can be positioned in other suitable sites. For example, the pacing device (210) can be placed in the coronary sinus, and a suitable electrode pair (e.g., electrodes (212, 214)) may be used to pace the ventricle.

The ablation device (220) may be introduced into an endocardial space of the left atrium (204) through an atrial septum via a trans-septal puncture. The distal portion of the ablation device (220) may include a set of electrodes (222, 224) configured to deliver ablation energy (e.g., pulse electric field energy) to tissue. In some embodiments, the electrodes (222, 224) of the ablation device (220) may be a set of independently addressable electrodes. Each electrode may include an insulated electrical lead configured to sustain a voltage potential of at least about 700 V without dielectric breakdown of its corresponding insulation. In some embodiments, the insulation on each of the electrical leads may sustain an electrical potential difference of between about 200 V to about 2,500 V across its thickness without dielectric breakdown. In some embodiments, the set of electrodes may include a plurality of electrodes. The plurality of electrodes may be grouped into one or more anode-cathode subsets such as, for example, a subset including one anode and one cathode, a subset including two anodes and two cathodes, a subset including two anodes and one cathode, a subset including one anode and two cathodes, a subset including three anodes and one cathode, a subset including three anodes and two cathodes, and/or the like. While two electrodes (222, 224) are depicted, it can be appreciated that ablation device (220) can include one or more additional electrodes, where one or more sets of electrodes can be configured with opposite polarities to deliver pulsed electric fields to ablate tissue.

Figure 3A:
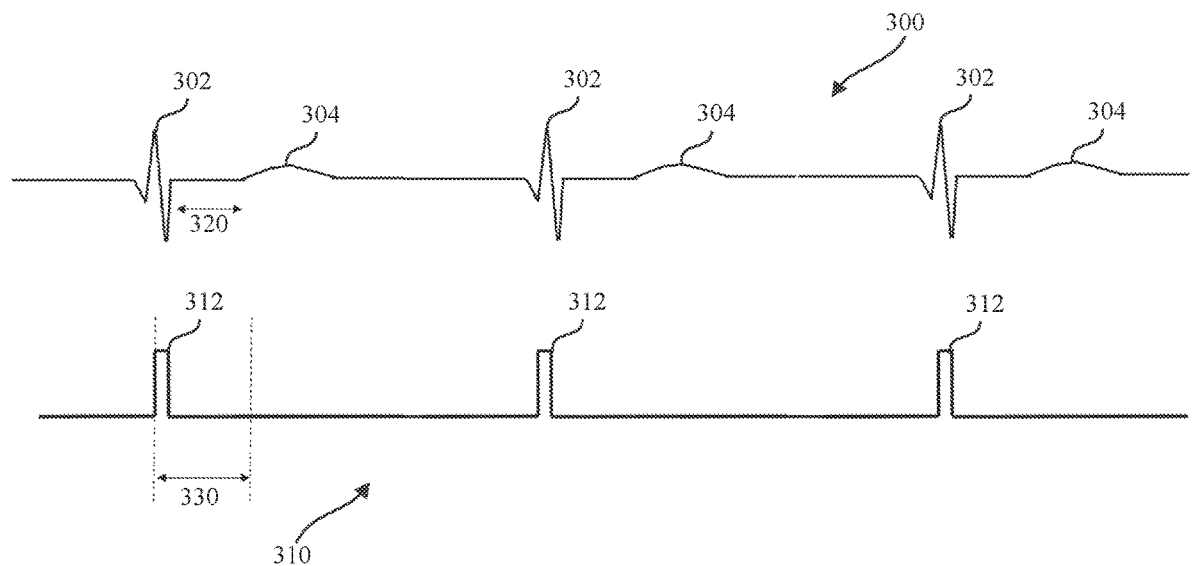
FIGS. 3A and 3B are schematic illustrations of a time sequence of electrocardiograms and cardiac pacing signals, according to embodiments.
Figure 3B:
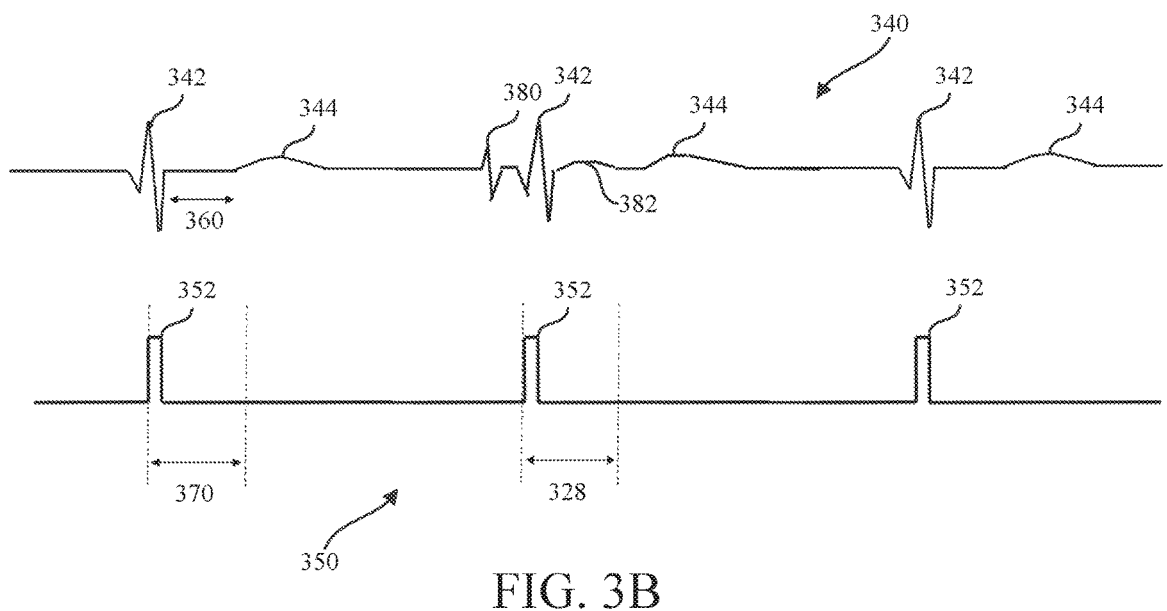

The operation of systems and devices for detection of pacing signals and/or ectopic activity can be understood with reference to FIGS. 3A and 3B, which schematically illustrate a time series of periodic pacing pulses with cardiac activity, according to embodiments described herein.

FIG. 3A is a schematic illustration of a time sequence of an electrocardiogram (300) and cardiac pacing signal (310). The pacing signal (310) may comprise a set of periodic pacing pulses (312). For example, the pacing pulse (312) may comprise a rectangular pulse having a width of between about 1 ms and about 5 ms. In some embodiments, the pacing pulses (312) may be delivered using any of the pacing devices (e.g., pacing devices (130, 210)) described herein. For example, the pacing pulse (312) may be delivered via pacing electrodes (212, 214) of pacing catheter (210). In response to the pacing pulses (312), the cardiac cycle of the heart may synchronize with the pacing pulses (312). For example, the QRS waveforms (302) in FIG. 3A are synchronized with respective pacing pulses (312). The T-wave (304) that follows the QRS waveform (302) corresponds to the start of repolarization occurring in the cardiac myocytes. As such, delivery of an ablation pulse waveform after the T-wave begins may cause complications (e.g., atrial and/or ventricular fibrillation) and therefore be avoided. The time period (330) that starts from the onset of the pacing pulse (312) and ends before the T-wave (304) represents a safe time window during which an ablation pulsed electric field can be delivered to the heart. In some embodiments, ablation pulse waveforms are delivered within a refractory period (320) of the cardiac cycle following the pacing pulse (312). In some embodiments, more than one cardiac chamber may be paced (e.g., simultaneous pacing of an atrium and a ventricle) to establish a common refractory period for more than one cardiac chamber. In such embodiments, the pacing pulse (312) can be delivered during a common refractory period or overlap in the refractory period associated with each cardiac chamber.

FIG. 3B is a schematic illustration of a time sequence of an electrocardiogram (340) and cardiac pacing signal (350). Similar to the periodic pacing pulses (312) shown in FIG. 3A, each pacing pulse (352) may comprise a rectangular pulse having a width of between about 1 ms and about 5 ms, and may be delivered using any of the pacing devices (e.g., pacing devices (130, 210)) described herein. For example, the pacing pulse (352) may be delivered via pacing electrodes (212, 214) of pacing catheter (210). In response to the pacing pulses (352), the natural pacing function of the heart may synchronize with the QRS waveforms (342). The T-wave (344) that follows the QRS waveform (342) corresponds to the start of repolarization in the cardiac myocytes. Without ectopic activity, the time period (370) that starts from the onset of the pacing pulse (352) and ends before the T-wave (344) represents a safe time window during which an ablation pulsed electric field can be delivered to the heart. The electrocardiogram (340) includes a refractory period (360) during which ablation can be delivered. With ectopic activity, e.g., as represented by an ectopic pulse (380) in the electrocardiogram (340), delivery of pulsed electric field ablation during the time period (370) may induce fibrillation. As depicted in FIG. 3B, an ectopic pulse or complex (380) can precede the QRS waveform (342) synchronized with the pacing pulse (352). The ectopic pulse (380) may generate an ectopic T-wave (382) that precedes the T-wave (344) of the QRS waveform (342). If a pulse waveform is delivered during the period (328) following the ectopic pulse (380), the pulse waveform may overlap the ectopic T-wave (382) and thereby cause complications, e.g., by inducing fibrillation. Accordingly, it can be desirable to detect the occurrence of an ectopic complex such as ectopic pulse (380) during an ablation procedure (e.g., in real-time), and upon detection, interrupt delivery of pulsed electric field ablation pulses. As described in more detail herein, systems, devices, and methods described herein can enable ectopic beats to be detected in real-time (e.g., during a pacing and/or ablation process) and delivery of ablation energy to tissue to be controlled (e.g., interrupting delivery of pulse waveform pulses) in response thereto. For example, such systems, devices, and methods can be configured for automated detection of ectopic ECG activity such that, if an ectopic beat is detected, subsequent ablation delivery can be terminated, e.g., until a user has repositioned devices, adjusted pacing parameters, or made other clinical adjustments to obtain a ECG waveform in synchrony with pacing pulses that does not include ectopic activity.

Figure 4:
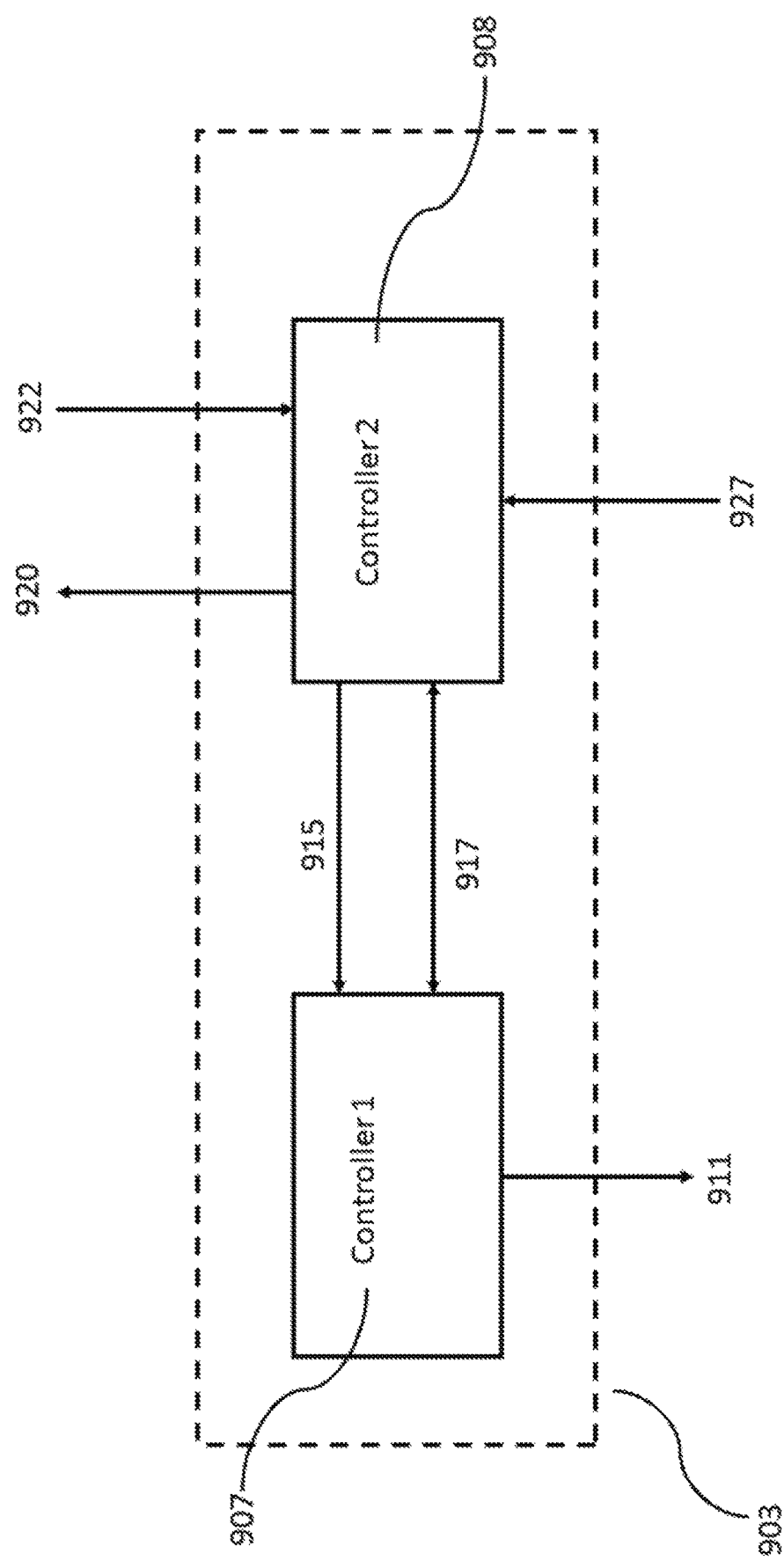
FIG. 4 schematically depicts a device for generating pulsed electric field ablation, according to embodiments.

FIG. 4 schematically depicts an example apparatus (903) for generating pulsed electric field energy for tissue ablation. The apparatus (903) can include components that are structurally and/or functionally similar to those of the apparatus (120), described above with reference to FIG. 1. In an embodiment, the apparatus (903) includes at least two controllers or processors (907, 908). The controller (907) can be configured to generate a waveform for pulsed electric field ablation via an ablation output (911) that connects to an energy delivery device such as, for example, an ablation catheter (e.g., ablation device (110)).

The controller (908) can be configured to generate a pacing stimulus and send that pacing stimulus to an intracardiac pacing catheter or similar medical device (e.g., pacing device (130)) via pacing output (920). The controller (908) can further send an indication (915) of the pacing stimulus to the controller (907), such that the delivery of the pulsed electric field energy can be synchronized with the cardiac pacing. The controllers (907, 908) can be operatively coupled to one another, e.g., by a communication bus (917). By synchronizing the delivery of the pulsed electric field ablation energy to the pacing stimulus, the apparatus (903) can ensure that pulsed electric field energy is delivery to sensitive anatomical structures (e.g., a cardiac chamber) during a refractory period, as described above, thereby avoiding the risk of inducing an arrhythmia such as a fibrillation event.

In some instances, an ectopic beat can arise by autonomous generation from a cardiac chamber. As described above, pulsed electric field ablation delivered during periods of ectopic activity can increase the risk of inducing an arrhythmia. Accordingly, it can be desirable to detect such ectopic activity. To detect such activity, cardiac signals (e.g., ECG recordings) from an intracardiac electrode pair can be sent as sensing signals (922) to the controller (908). The controller (908) can be configured to analyze the cardiac signals for ectopic beats. When the controller (908) detects an ectopic beat, the controller (908) can be configured to communicate with the controller (907) responsible for generating the ablation waveform, e.g., via communication bus (917), to halt the delivery of the pulsed electric field energy. For example, the controller (908) can send a signal to halt or interrupt ablation to the controller (907) in response to detecting ectopic activity.

In some embodiments, the apparatus (903) can be configured to confirm pacing capture prior to delivery of pulsed electric field energy. For example, the apparatus (903) via controller (908) can analyze the sensed cardiac signals (922) and communicate with controller (907) to deliver ablation upon confirmation of pacing capture. In some embodiments, the apparatus (903) can be equipped with a user interface for confirming pacing capture, e.g., via a manual input (927) by a user. For example, the apparatus (903) can include a display that displays the pacing signal and cardiac signal to allow a user to confirm pacing capture and indicate such confirmation to the apparatus (903) (e.g., by pushing a button on the user interface). In some embodiments, the apparatus (903) can analyze the sensed cardiac activity, and if such is found to not be in synchrony with the pacing stimulus, not perform ablation delivery and/or inform a user that pacing capture is absent (e.g., via user interface or a message). The user and/or apparatus (903) can then modify the pacing conditions, e.g., attempt pacing capture at a different rate, or move the pacing catheter to a location or position with better anatomical engagement.

Figure 5:
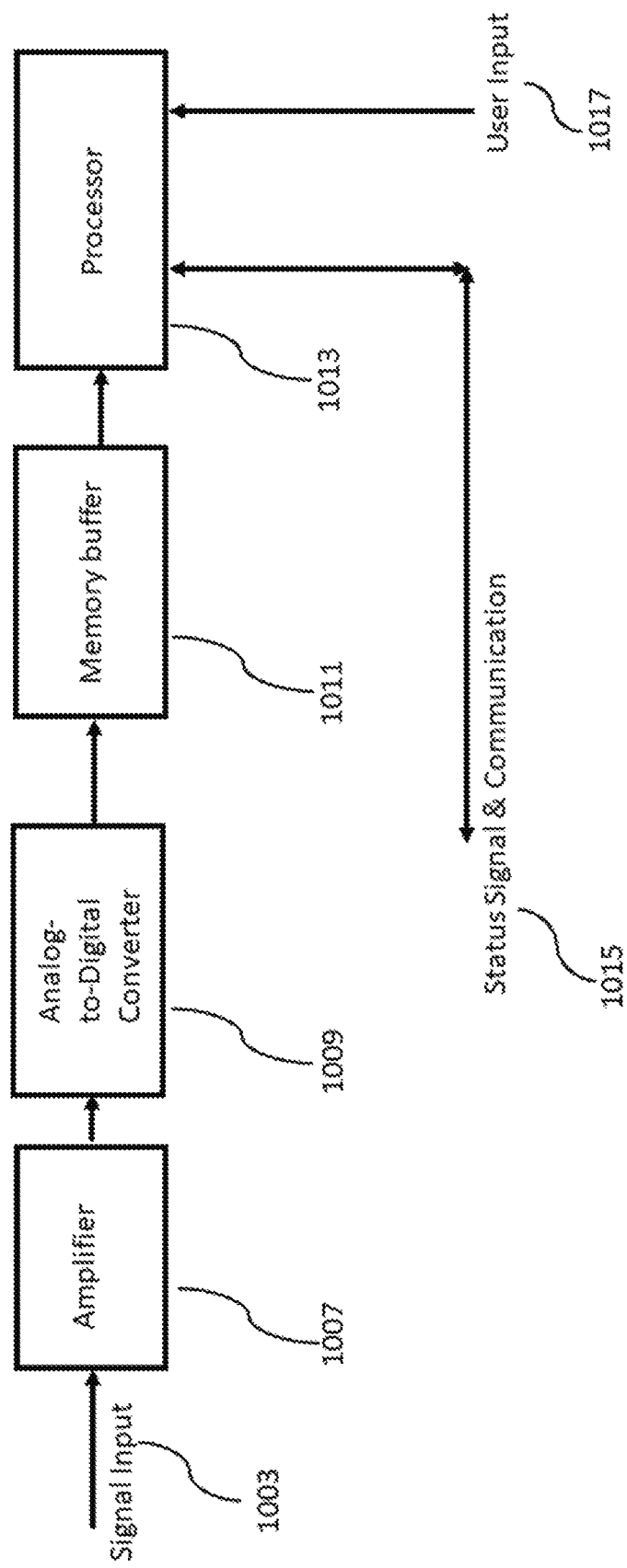
FIG. 5 depicts components of a device for detecting cardiac activity, according to embodiments.

FIG. 5 schematically depicts an example flow of a signal (e.g., an ECG signal) through one or more components of a controller, such as, for example, controller (908) depicted in FIG. 4, in more detail. As depicted, an incoming signal (1003) (e.g., raw analog cardiac activity signal captured using intracardiac electrodes) can be received at an amplifier (1007). Amplifier (1007) may be configured to amplify the signal (1003) for digitization by an analog-to-digital converter (ADC) (1009). The ADC (1009) can output the processed cardiac data as a stream of digitized data. The digitized data may be stored or buffered as cardiac activity data in memory (1011). The processor (1013) may analyze and/or process the buffered cardiac data in segments of predetermined size (e.g., windowed data) for ectopic cardiac activity.

In some embodiments, the analysis can be based on comparing data to one or more threshold values, e.g., predetermined and preprogrammed into the processor (1013) and/or provided by a user via a user input (1017) to a user interface (e.g., a touchscreen monitor or other type of monitor, etc.). Based on the analysis, the processor (1013) may be configured to output a cardiac activity status to a controller for generating an ablation waveform or pulse generator controller (e.g., the signal generator (122) or the controller (907)).

The signal (1015) may indicate one or more of pacing capture status (e.g., ECG signal in/out of synchrony with a pacing pulse) and ectopic cardiac activity status. For example, if pacing capture is not detected, the processor (1013) can send a corresponding status signal (1015) indicating a lack of pacing capture to a pulse generator controller. The processor (1013) and/or the pulse generator controller can then alert a user, e.g., through a user interface, that pacing capture is not present and ablation cannot be performed. The user can then take appropriate action such as, for example, halting an ablation procedure and/or reconfiguring the system. For example, the user may reposition one or more of an ablation device (e.g., ablation device (110)) and/or pacing device (e.g., pacing device (130)), and/or adjust other system parameters. If pacing capture is confirmed by the processor (1013), a different signal (1015) indicating readiness for ablation can be sent to the pulse generator controller, whereupon the pulse generator controller may be configured to initiate ablation when requested by a user. In some embodiments, systems and devices described herein may measure cardiac activity before, during, and after ablation energy delivery.

Additionally or alternatively, the processor (1013) can detect ectopic beats. For example, if pacing capture is confirmed but an ectopic beat is detected, the processor (1013) can be configured to send a signal (1015) to the pulse generator controller such that the pulse generator controller does not generate a pulse waveform for ablation. The processor (1013) and/or pulse generator controller can inform a user to the presence of ectopic beats and that ablation cannot be performed, e.g., via a user interface. The processor (1013) can also continue to monitor the sensed ECG signal for ectopic beats that may occur during ablation. If such ectopic beats are detected, the processor (1013) can send a signal (1015) to the pulse generator controller indicating that ablation should be paused or interrupted. The pulse generate controller, in response to receiving the signal (1015) can then half further ablation delivery, e.g., until the user adjusts the system and/or no ectopic beat activity is detected.

Methods

Also described here are methods for detecting ectopic cardiac activity during a tissue ablation process performed in a heart chamber using the systems and devices described above. The heart chamber may be the left atrial chamber and include its associated pulmonary veins. Generally, the methods described here include introducing and disposing a pacing device (e.g., pacing device (130), pacing device (210)) in contact with one or more heart chambers. The pacing device may measure cardiac activity and deliver a pacing signal to the heart using a cardiac stimulator or other processor (e.g., cardiac stimulator (128), controller (908), processor (1013)). The measured signals may be processed and analyzed to detect pacing capture and/or ectopic cardiac activity that may interfere with tissue ablation, e.g., by such processor and controllers as described herein. An ablation device (e.g., ablation device (110), ablation device (220)) may be introduced and disposed in contact with one or more pulmonary vein ostial or antral regions. A pulse waveform may be delivered by one or more electrodes (e.g., electrodes (112), electrodes (222, 224)) of the ablation device to ablate tissue. In some embodiments, detection of autonomously generated ectopic cardiac activity may drive prompt interruption of ablation energy delivery, thereby reducing the risk of inducing an arrhythmia (e.g., fibrillation). Furthermore, a cardiac pacing signal (e.g., delivered by a pacing device (e.g., pacing device (130), pacing device (210)) may synchronize the delivered pulse waveforms with the cardiac cycle. By synchronizing the delivery of ablation energy to a pacing stimulus (e.g., during a refractory period), the risk of inducing an arrhythmia such as fibrillation may be further reduced.

Additionally or alternatively, the pulse waveforms may include a plurality of levels of a hierarchy to reduce total energy delivery, e.g., as described in International Application Serial No. PCT/US2019/031135, filed on May 7, 2019, and titled "SYSTEMS, APPARATUSES AND METHODS FOR DELIVERY OF ABLATIVE ENERGY TO TISSUE," the contents of which are hereby incorporated by reference in its entirety. The tissue ablation thus performed may be delivered in the absence of ectopic cardiac activity and in synchrony with paced heartbeats to reduce the risk of atrial and/or ventricular fibrillation and damage to healthy tissue. It should be appreciated that any of the ablation devices described herein (e.g., ablation device (110), ablation device (220)) may be used to ablate tissue using the methods discussed below as appropriate.

In some embodiments, the ablation devices described herein (e.g., ablation device (110), ablation device (220)) may be used for epicardial and/or endocardial ablation. Examples of suitable ablation catheters are described in International Application Serial No. PCT/US2019/014226.

Figure 6:
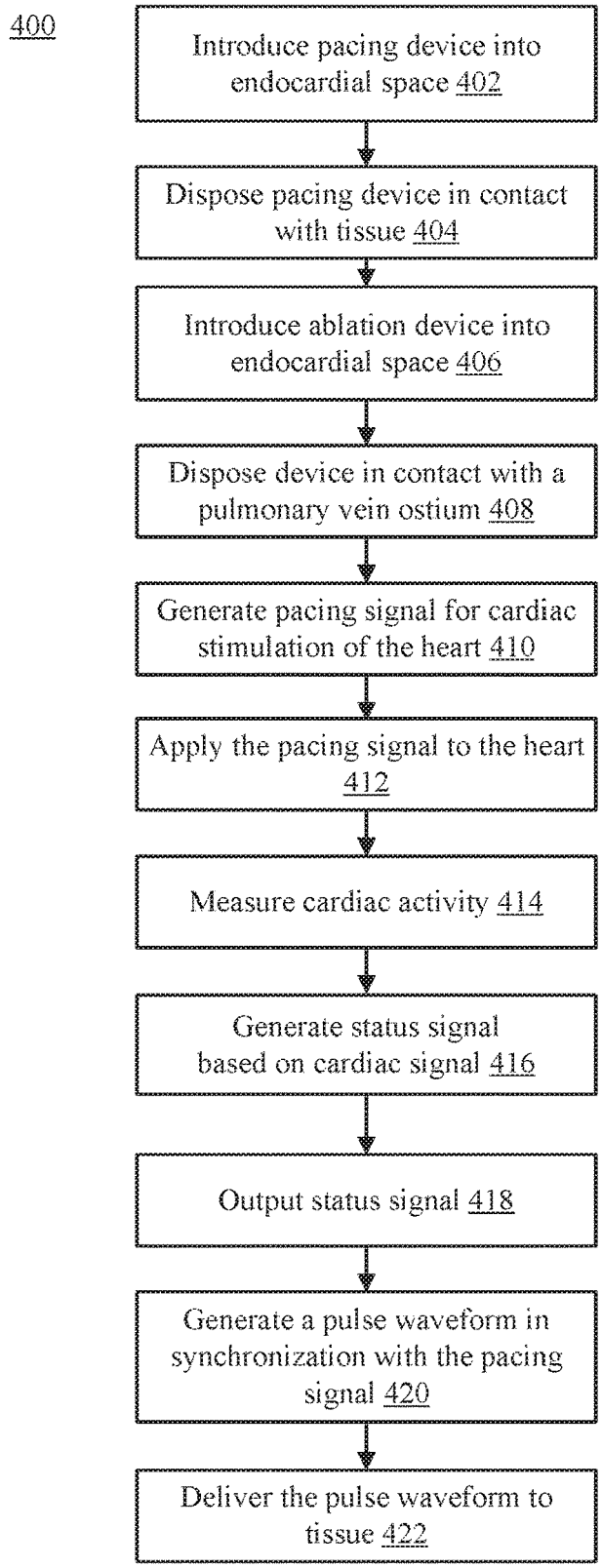
FIG. 6 illustrates a method for tissue ablation, according to embodiments.

FIG. 6 is an example method (400) of tissue ablation. In some embodiments, the voltage pulse waveforms described herein may be applied during a refractory period of the cardiac cycle so as to avoid disruption of the sinus rhythm of the heart. The method (400) includes introduction of a pacing device (e.g., pacing device (130, 210)) into an endocardial space, e.g., of a right ventricle, at (402). The pacing device may be advanced to be disposed in contact with the cardiac tissue, at (404). For example, sensor electrodes configured for cardiac activity measurement (e.g., ECG signals) and pacing electrodes configured for delivering pacing signals may be disposed in contact with an inner surface of the right ventricle. An ablation device (e.g., ablation device (110, 220)) may be introduced into an endocardial space, e.g., of a left atrium, at (406). The ablation device may be advanced to be disposed in contact with a pulmonary vein ostium, at (408). In some embodiments, a pacing signal may be generated by a cardiac stimulator (e.g., cardiac stimulator (128)) for cardiac stimulation of the heart, at (410). The pacing signal may then be applied to the heart, at (412), using the pacing electrodes of the pacing device. For example, the heart may be electrically paced with the pacing signal to ensure pacing capture to establish periodicity and predictability of the cardiac cycle. One or more of atrial and ventricular pacing may be applied. Examples of applied pacing signals relative to patient cardiac activity are described in more detail herein with respect to FIGS. 3A and 3B. One or more electrodes of the pacing device and/or ablation device may further measure cardiac activity (e.g., ECG signal) corresponding to electrical cardiac activity of the heart, at (414). In some embodiments, cardiac activity may be measured before, during, and/or after cardiac stimulation and tissue ablation.

Figure 7:
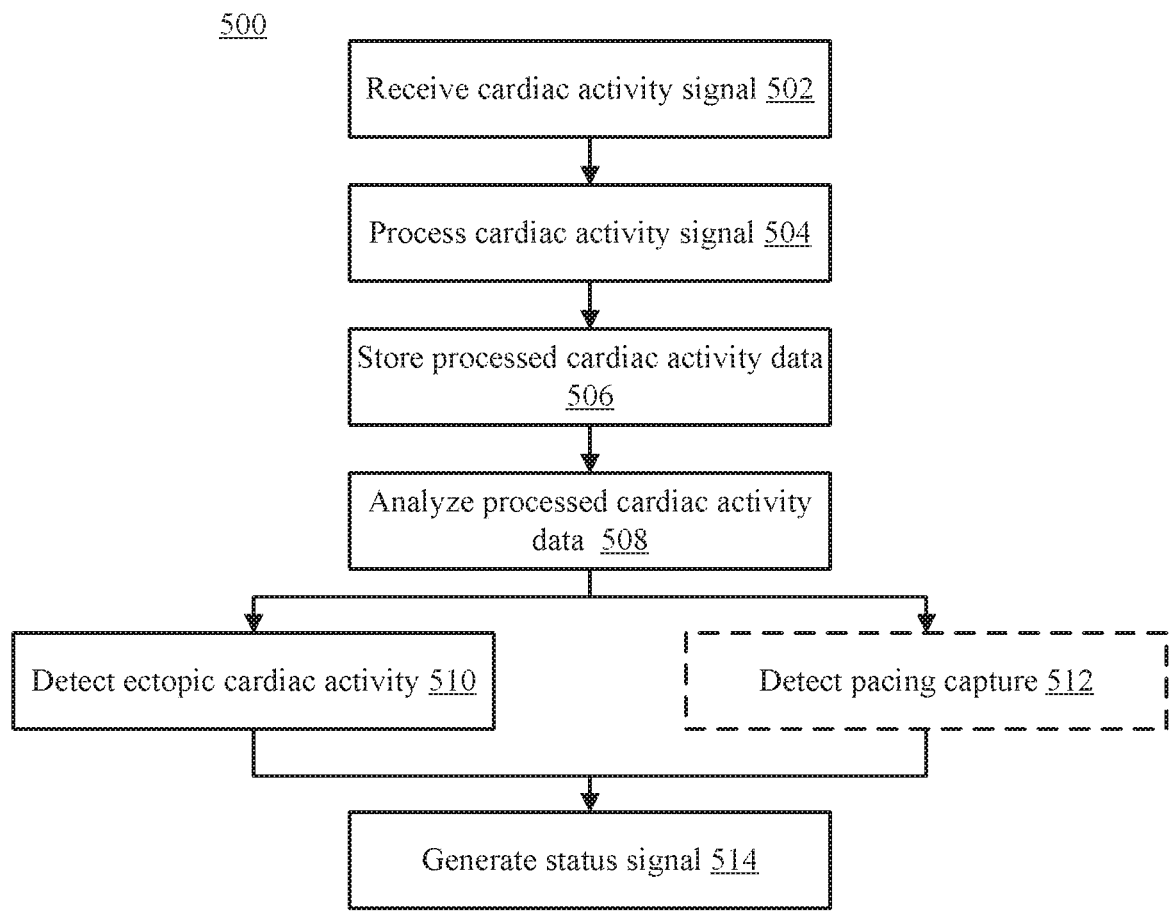
FIG. 7 illustrates a method for detecting ectopic cardiac activity, according to embodiments.
Figure 9:
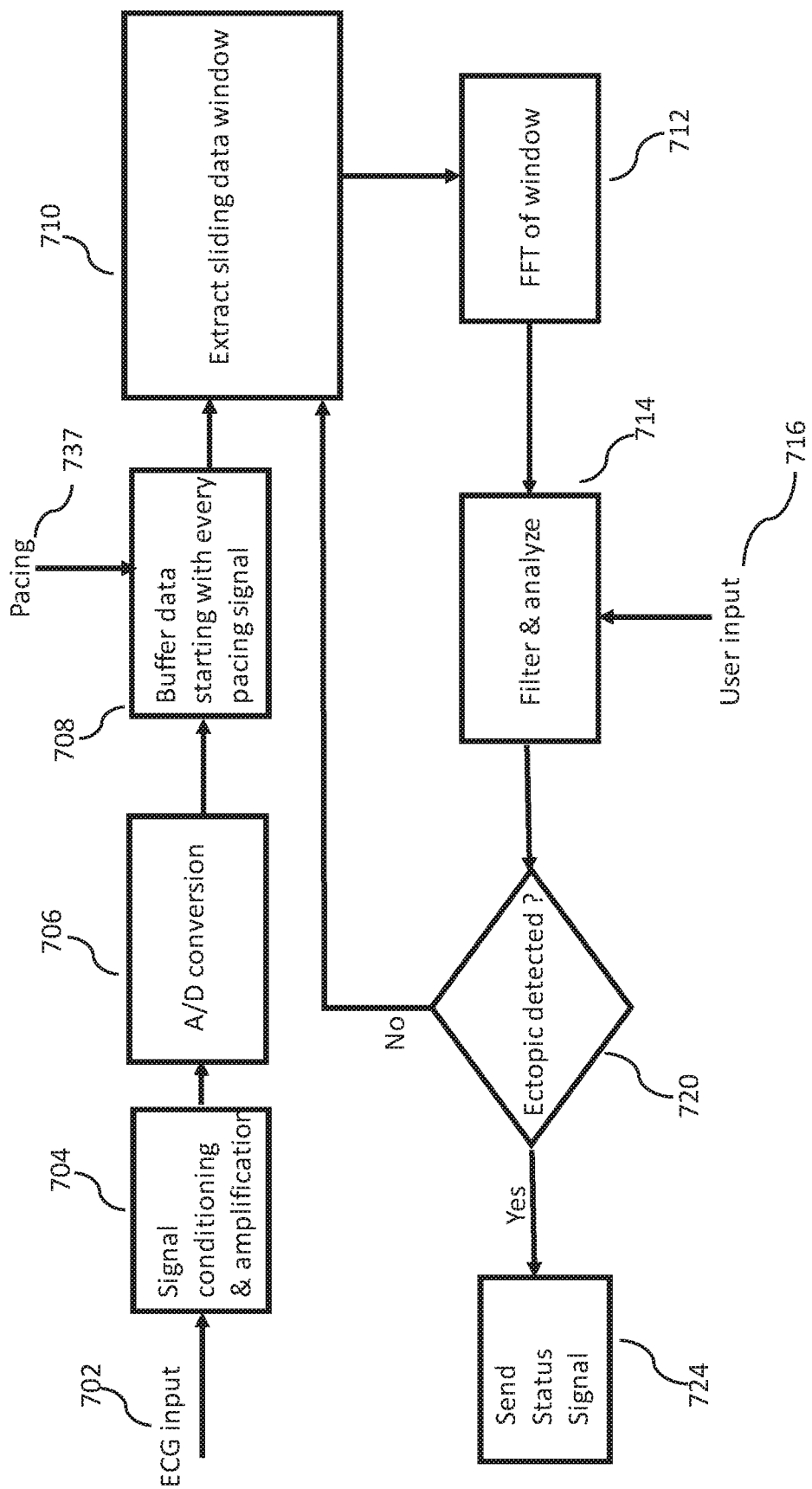
FIG. 9 illustrates a method for detecting ectopic cardiac activity, according to embodiments.
Figure 10:
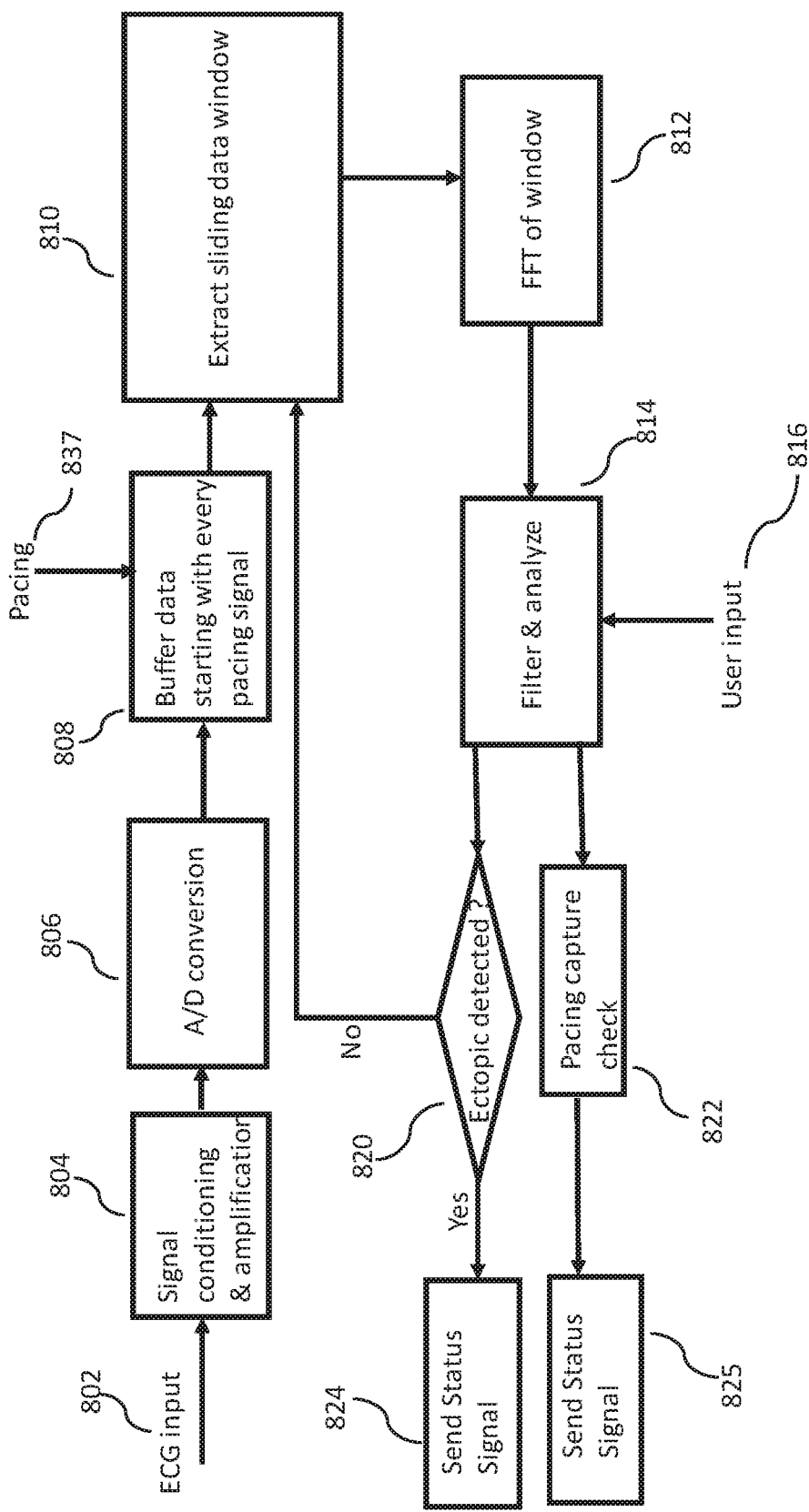
FIG. 10 illustrates a method for detecting ectopic cardiac activity and confirming pacing capture, according to embodiments.

An apparatus (e.g., apparatus (120, 903)) can process and/or analyze the cardiac signal sensed by the one or more electrodes. Based on analysis of the cardiac data, a status signal may be generated, at (416). The status signal may indicate a status of one or more of pacing capture and/or ectopic cardiac activity. For example, FIGS. 7, 9, and 10 provide more detailed examples of detecting ectopic cardiac activity. The status signal may be output to one or more of a signal generator (e.g., signal generator (122)) or any processor associated with an ablation device (110, 220) and/or output to a user interface, at (418). Based on the status signal, the signal generator may or may not generate a pulse waveform, at (420), e.g., based on predetermined criteria as described herein. For example, the pulse waveform may be generated in synchronization with the pacing signal (e.g., during a refractory period) when the status signal indicates one or more of a lack of ectopic cardiac activity (e.g., ectopic beat) in the cardiac data and confirmation of pacing capture (e.g., synchronization between the pacing signal and the cardiac cycle). For example, when pacing capture is observed over several heartbeats without ectopic cardiac activity, then the signal generator may generate a pulse waveform upon user (e.g., operator) activation. Conversely, the signal generator may be configured to inhibit pulse waveform generation and/or output an alert to the user when the cardiac activity status indicates one or more of ectopic cardiac activity (e.g., ectopic beat) in the cardiac data and/or an absence of pacing capture.

In some embodiments, pacing capture may be automatically confirmed by apparatuses described herein (e.g., apparatus (120, 903)) based on the received cardiac data. Additionally or alternatively, pacing capture may be confirmed by a user, e.g., after viewing an output of the pacing signal and cardiac signal data. For example, the user may confirm pacing capture using a user interface (e.g., an input/output device such as a touch screen monitor or other type of monitor) based on a cardiac activity output on a display. If the signal generator and/or processor, or the user viewing the displayed cardiac output, determines that there is one or more of ectopic cardiac activity and an absence of pacing capture, pulse waveform generation may be prohibited and the user may be prompted to adjust system parameters by, for example, repositioning the pacing device to improve tissue engagement and/or modify pacing signal parameters (e.g., pulse width, pulse amplitude, pulse frequency, etc.).

The generated pulse waveform may be delivered to tissue, at (422). In some embodiments, a voltage pulse waveform may be applied in a common refractory time period associated with atrial and ventricular pacing signals. Depending on the cardiac data that is captured and/or other parameters associated ablation delivery, the pulse waveform may be generated with a time offset with respect to the indication of the pacing signal. For example, the refractory time period may be offset from the pacing signal by predetermined time period, and the ablation device can be configured to deliver the pulses during the refractory time period that is offset from the pacing signal. In some embodiment, the voltage pulse waveform(s) may be applied over a series of heart-beats over corresponding refractory time periods (e.g., common refractory periods).

In some embodiments, the pulse waveform may be delivered to pulmonary vein ostium of a heart of a patient via one or more splines of a set of splines of an ablation device (e.g., ablation device (110, 220). In other embodiments, voltage pulse waveforms as described herein may be selectively delivered to electrode subsets such as anode-cathode subsets for ablation and isolation of the pulmonary vein. For example, a first electrode of a group of electrodes may be configured as an anode and a second electrode of the group of electrodes may be configured as a cathode. These steps may be repeated for a desired number of pulmonary vein ostial or antral regions to have been ablated (e.g., 1, 2, 3, or 4 ostia). Suitable examples of ablation devices and methods are described in International Application No. PCT/US2019/014226.

FIG. 7 is an example method (500) for detecting ectopic cardiac activity. In some embodiments, one or more steps of the method (500) may be performed by any one of the apparatuses described herein (e.g., apparatus (120, 903)), or any suitable processor associated with devices and methods described herein. The method (500) includes receiving a cardiac activity signal corresponding to electrical cardiac activity (e.g., ECG waveforms) of the heart, at (502). For example, the cardiac activity signal may include analog data received continuously from a set of electrodes (e.g., electrodes (216, 218)) of a pacing device (e.g., pacing device (210)) in contact with a chamber of a heart (e.g., the right ventricle). In some embodiments, a processor (e.g., controller (908), processor (1013)) or other processor associated with an ablation device may receive the cardiac activity signal and perform ectopic cardiac activity detection. The raw cardiac activity signal may be received and processed, at (504), to generate processed cardiac activity data. For example, signal processing may include signal conditioning (e.g., filtering), amplification, and digitization (e.g., using an analog-to-digital converter (ADC)) to generate processed cardiac activity data. For example, the cardiac activity signal may be sampled at a frequency in the range of about 1 kHz or sampling time intervals of about 1 ms and stored at a predetermined resolution (e.g., discrete time series of 16-bit signed integer data). A sampling time interval of 1 ms corresponds to a Nyquist frequency of 500 Hz. The processed cardiac activity data is stored in memory, at (506), such as a buffer. In some embodiments, the buffer clears the stored cardiac data based on a received pacing signal. For example, the buffer deletes the previously stored cardiac data upon receiving the next pacing pulse. In some embodiments, the pacing signal may include a predetermined pacing frequency.

The processed cardiac activity data may be analyzed for one or more of ectopic cardiac activity and pacing capture, at (508). For example, the processed cardiac activity data can be analyzed by extracting sliding windows of the data, and each sliding window can be evaluated for ectopic cardiac activity, e.g., using discrete Fourier transform methods. Specific implementations of such analysis are further described with reference to FIGS. 9 and 10. Optionally, in some embodiments, the processed cardiac activity data can be analyzed to confirm pacing capture, at (512).

In some embodiments, ectopic cardiac activity detection, at (510), may be performed in parallel with pacing capture detection, at (512). In other embodiments, pacing capture detection, at (512), can be performed prior to performing ectopic cardiac activity detection, at (510).

A status signal may be generated, at (514), based on the results of the detected ectopic cardiac activity and/or pacing capture. In some embodiments, the status signal may be output to one or more components of an ablation apparatus (e.g., apparatus (120)), including, for example, a signal or pulse generator (e.g., signal generator (122)) and/or another compute device. For example, a user interface (e.g., a user interface such as a display, including in an apparatus (120)) of a tissue ablation system may be configured to display an indication confirming pacing capture (e.g., "Pacing Capture Confirmed") and display an "Ablation" icon configured to allow a user to initiate delivery of ablation energy to tissue. In some embodiments, the cardiac activity status need not be output to a user if pacing capture is confirmed and no ectopic beat is detected. Rather, an indication (e.g., an audio and/or visual alarm) can be made when either pacing capture cannot be confirmed or when an ectopic beat is detected.

FIGS. 9 and 10 are flow charts depicting example methods of detecting ectopic cardiac activity and/or confirming pacing capture. One or more steps of the methods may be performed by any one of the apparatuses described herein (120, 903), or any suitable processor associated with devices and methods described herein. As depicted in FIG. 9, a method of detecting ectopic cardiac activity includes receiving an ECG input, at (702). The ECG input can be, for example, ECG signal data received from a set of electrodes of a pacing device (e.g., electrodes (216, 218) of pacing device (210)). The ECG signal can be an analog signal. The ECG input can be processed, at (704), e.g., by conditioning (e.g., filtering) and/or amplifying the signal. The ECG signal can be converted from analog to digital, e.g., using an ADC, at (706). In some embodiments, the data can be sampled at a frequency to achieve sufficient resolution, e.g., at a frequency of about 1 kHz or sampling time intervals of about 1 ms, and stored as bit-based integer data (e.g., 16-bit signed integer data, 32-bit signed integer data, etc.). The digitized or sampled data can be stored in a memory (e.g., memory (126, 1011)), at (708). For example, the data can be buffered starting with each pacing signal such that each set of buffered data is associated with a single heart beat or cardiac cycle. The pacing signal data can be provided, e.g., by a pacing device (e.g., pacing device (130, 210)) and/or processor associated with a pacing device (e.g., processor (124, 908, 1013)), at (737). When a later set of data associated with a second pacing signal is received, the existing buffer can be cleared and this new data associated with the second pacing signal can be stored in the buffer.

At (710), the buffered data may be analyzed by extracting sliding windows of predetermined length. For example, beginning at a time interval equal to the pacing pulse width after the leading edge of the pacing pulse, the buffered data is extracted in sliding windows of a predetermined length (e.g., a window of 220 data points), which corresponds to a frequency resolution of approximately 4.54 Hz. The sliding window can start after the pacing pulse (i.e., after a time interval equal to the pulse width), and be advanced in discrete steps, e.g., with a step size equal to a preset number of sampling time intervals such as 10 sampling time intervals. The number of sliding windows extracted from the buffered data per cardiac cycle may depend on one or more parameters, such as, for example, a length between pacing pulses, window length, and/or step size, each of which can be a predetermined parameter.

A discrete Fourier Transform (e.g., Fast Fourier Transform) may be performed for each sliding window, at (712). The result of the Fourier Transform (e.g., amplitude) may be filtered (e.g., by a smoothing filter) to output a function $f$ corresponding to a local average over a set of neighboring values around each data point, at (714). Local peaks in function $f$ may be identified over a subrange of the data of each sliding window. For example, if a sliding window had a length of 220 data points, a subrange ranging from about 12 to about 100 ($12^{th}$ data point to $100^{th}$ data point) can be used, which corresponds to a frequency band from about 54 Hz to about 454 Hz. While these specific sliding window lengths and frequency bands are provided as examples, it can be appreciated that other sliding window lengths and frequency bands can be used, e.g., depending on desired parameters, processing capability, etc. Analysis of peaks within the frequency band can be used to determine whether ectopic cardiac activity is present, at (720).

The processed ECG data within each sliding window can be used to detect ectopic cardiac activity. In an embodiment, an ectopic beat may be detected based on a comparison between a ratio of a peak value ($a_p$) of $f$ over the predetermined interval (or subrange or frequency band) to the maximum value ($a_{max}$) of $f$ up to the Nyquist frequency to a predetermined threshold t. In some embodiments, an ectopic beat may be detected in the sliding window when the ratio $a_p/a_{max}$ is greater than t. Because ectopic beats increase the amount of certain frequencies in ECG signals, detection can be accomplished by identifying instances where a greater than normal amount of a frequency is present in the sampled cardiac data. In some embodiments, t may be between about 0.01 and about 0.25, between about 0.01 and about 0.2, between about 0.01 and about 0.15, including all sub-values and ranges in-between. In some embodiments, the user may input t into a user interface of a tissue ablation system, at (716). The threshold t can represent a sensitivity of the system, i.e., a system with a lower threshold t would have greater sensitivity than a system with higher threshold t.

When an ectopic beat is not detected in a particular sliding window (720: NO), the process continues onto the next sliding window. When an ectopic beat is detected (720: YES), then a status signal can be generated, at (724), e.g., that notifies a compute device and/or a user of the ectopic activity, as described above with reference to (514) in FIG. 7.

In some embodiments, received ECG data can be used to confirm pacing capture. For example, as depicted in FIG. 10, an example method for detecting ectopic beats and confirming pacing capture is depicted. Similar to the method depicted in FIG. 9, an ECG input can be received, at (802). At (804), the ECG input can be processed, e.g., by conditioning (e.g., filtering) and/or amplifying the signal. At (806), the ECG signal can be converted from analog to digital, e.g., using an ADC. At (808), the digitized data can be stored in a memory (e.g., memory (126)). For example, the digitized data can be buffered in the memory starting with each pacing signal such that each set of buffered data is associated with a single heart beat or cardiac cycle.

At (810), the buffered data may be analyzed by extracting sliding windows of the data, each sliding window having a predetermined length and being advanced in discrete steps through the buffered data. Detection of ectopic beats, e.g., via a discrete Fourier Transform of the data, at (812), filtering and analysis of the data, at (814), and detection of peaks in the Fourier Transform data that is greater than a preset threshold, at (820), can be similar to that described in FIG. 9. In some embodiments, such detection can be based on a user input (816).

With ECG data being available, pacing capture can also be confirmed, at (822). To confirm pacing capture, a subset of sampled data can be extracted from the ECG data at the start of the pacing signal, as indicated by (837). For example, ECG data associated with a predetermined time interval T (e.g., a pacing pulse duration) starting from onset of a pacing pulse can be extracted. For example, the time period may have a length of between about 5 ms and about 50 ms. Accordingly, the subset of sampled data can, for example, include the first ten to fifty data points, depending on the sampling frequency and time interval T. A function g(t) may be defined by the subset of sampled data over the time interval T. In some embodiments, g(t) may represent an ECG signal scaled with respect to a maximum magnitude of the ECG signal over the time interval T. A set of moments (e.g., $M_0, M_1, \ldots, M_n$) of this function over the time interval T may be calculated, and can be tracked over a predetermined number of successive pacing periods (e.g., 1, 2, 3, 4, 5 successive pacing periods). The set of moments of the function can include, for example, the first three moments, which can be computed in discretized form as average values, or as other suitable integral representations (e.g., using the trapezoidal rule, Simpson's rule, or other integral measures) of g(t), tg(t), and $t^2$g(t) over the time interval T.

With the calculated moments, an average value $A_n$ of the nth moment over a set of i successive periods may be given by: $A_n = (M_n^1 + M_n^2 + M_n^3 + \ldots + M_n^i)/i$. Accordingly, for the first three moments over 5 successive pacing periods, the average values will be:

$$A_0 = (M_0^1 + M_0^2 + \ldots M_0^5)/5$$

$$A_1 = (M_1^1 + M_1^2 + \ldots M_1^5)/5$$

$$A_2 = (M_2^1 + M_2^2 + \ldots M_2^5)/5$$

A normalized difference between the average moment value $A_n$ and the moment value for the $i^{th}$ time period (e.g., for five time periods, i=1, 2, . . . , 5) of a given moment n may be calculated. For the first three moments (n=1, 2, 3), the following set of equations provide this normalized difference:

$$S_i = |A_0 - M_0^i|/A_0$$

$$T_i = |A_1 - M_1^i|/A_1$$

$$U_i = |A_2 - M_2^i|/A_2$$

where the $S_i$, $T_i$, and $U_i$ values are set to zero when the corresponding one of $A_0$, $A_1$, or $A_2$ are zero.

Confirmation of pacing capture may be detected based on the $S_i$, $T_i$, and $U_i$ values. For example, pacing capture over i predetermined time periods can be confirmed if for each non-zero value of $A_n$, its corresponding $S_i$, $T_i$, or $U_i$ value is less than a predetermined threshold or set of threshold values. For example, this threshold for the moment $M_0$ can be in the range between 0 and 0.1. A small deviation of the moment $M_n^i$ from the corresponding mean value indicates that the time-behavior of the ECG signal (viewed as a function of time) is morphologically consistent over successive pacing periods, thereby demonstrating pacing capture. In some embodiments, this threshold can be defined by a user, e.g., via input (816) provided by a user interface (e.g., of input/output device (127)). If pacing capture is confirmed (822), then this can be indicated, e.g., on a user interface by highlighting a "Pacing Capture Confirmed" indicator.

As described above with reference to FIG. 7, if no ectopic beat activity is detected, and pacing capture is confirmed, then an ablation device and processor(s) associated therewith (e.g., pulse generation controller (907) and other devices described herein) can be set to deliver pulsed electric field ablation. If ectopic beat activity is detected and/or pacing capture is not confirmed, then the ablation device and/or associated processor(s) can be deactivated and/or not set to delivery pulsed electric field ablation, for example, by activation of a suitable relay that disconnects the ablation device from the ablation generator. Specifically, if ectopic beat activity is detected, then it would be undesirable to deliver pulsed electric field ablation because it can cause fibrillation.

Figure 8:
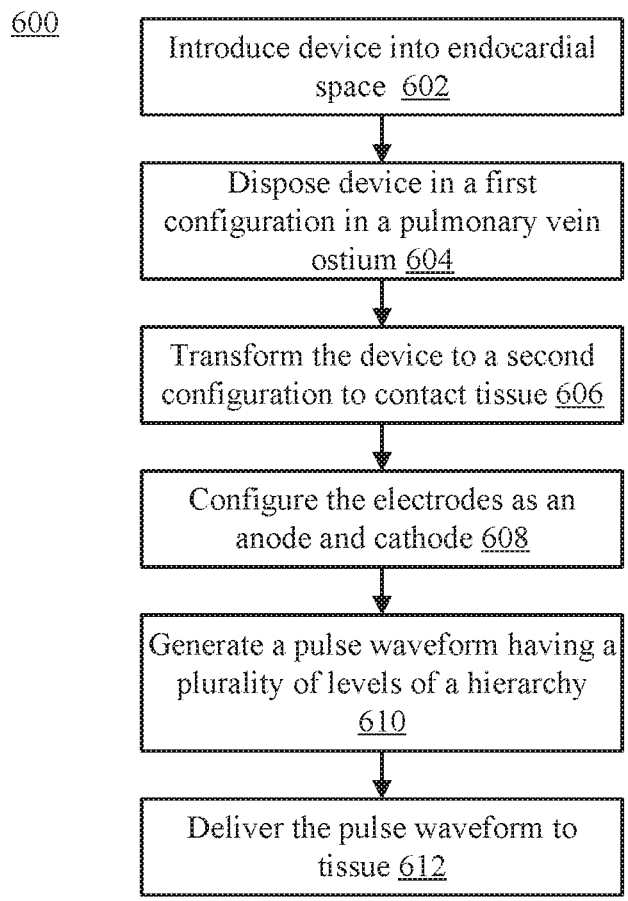
FIG. 8 illustrates a method for tissue ablation, according to embodiments.

In some embodiments, hierarchical voltage pulse waveforms having a nested structure and a hierarchy of time intervals as described herein may be useful for irreversible electroporation, providing control and selectivity in different tissue types. FIG. 8 is a flowchart (600) of an embodiment of a tissue ablation process. The method (600) includes the introduction of a device (e.g., ablation device (110, 220)) into an endocardial space, e.g., of a left atrium, at (602). The ablation device may be advanced to be disposed in a pulmonary vein ostium, at (604). In embodiments where the device may include a first and second configuration (e.g., compact and expanded), the device may be introduced in the first configuration and transformed to a second configuration to contact tissue at or near the pulmonary vein antrum or ostium, at (606), with further descriptions of suitable ablation devices provided in International Application No. PCT/US2019/014226. The ablation device may include electrodes and may be configured in anode-cathode subsets, at (608), as discussed in detail above. For example, a subset of electrodes of the devices may be selected as anodes, while another subset of electrodes of the device may be selected as cathodes, with the voltage pulse waveform applied between the anodes and cathodes.

A pulse waveform may be generated by a signal generator (e.g., signal generator (122)) and may include a plurality of levels in a hierarchy, at (610). A variety of hierarchical waveforms may be generated with a signal generator as disclosed herein. For example, the pulse waveform may include a first level of a hierarchy of the pulse waveform including a first set of pulses. Each pulse has a pulse time duration and a first time interval separating successive pulses. A second level of the hierarchy of the pulse waveform may include a plurality of first sets of pulses as a second set of pulses. A second time interval may separate successive first sets of pulses. The second time interval may be at least three times the duration of the first time interval. A third level of the hierarchy of the pulse waveform may include a plurality of second sets of pulses as a third set of pulses. A third time interval may separate successive second sets of pulses. The third time interval may be at least thirty times the duration of the second level time interval. The pulse waveform generated by the signal generator may be delivered to tissue using the ablation device, at (612). As described herein, if ectopic beat activity is detected or pacing capture is not confirmed, then the delivery of pulse waveform activity may be interrupted, e.g., at (608) or (610). Examples of pulse waveforms that can be used with the ablation devices described herein are provided in International Application No. PCT/US2016/57664, filed on Oct. 19, 2016, titled "Systems, apparatuses and methods for delivery of ablative energy to tissue," incorporated herein by reference in its entirety.

It is understood that while the examples herein identify separate monophasic and biphasic waveforms, it should be appreciated that combination waveforms, where some portions of the waveform hierarchy are monophasic while other portions are biphasic, may also be generated. A voltage pulse waveform having a hierarchical structure may be applied across different anode-cathode subsets (optionally with a time delay). As discussed above, one or more of the waveforms applied across the anode-cathode subsets may be applied during the refractory period of a cardiac cycle. The pulse waveform may be delivered to tissue. It should be appreciated that the steps described in certain figures may be combined and modified as appropriate.

It should be understood that the examples and illustrations in this disclosure serve exemplary purposes and departures and variations such as numbers of splines, number of electrodes, and so on can be built and deployed according to the teachings herein without departing from the scope of this invention. While specific parameters such as sampling frequency, time intervals and so on were given for exemplary purposes only in the description herein, it should be understood that other values of the various parameters can be used as convenient for the application by those skilled in the art based on the teachings presented in this disclosure.

As used herein, the terms "about" and/or "approximately" when used in conjunction with numerical values and/or ranges generally refer to those numerical values and/or ranges near to a recited numerical value and/or range. In some instances, the terms "about" and "approximately" may mean within ±10% of the recited value. For example, in some instances, "about 100 [units]" may mean within ±10% of 100 (e.g., from 90 to 110). The terms "about" and "approximately" may be used interchangeably.

Some embodiments described herein relate to a computer storage product with a non-transitory computer-readable medium (also may be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also may be referred to as code or algorithm) may be those designed and constructed for the specific purpose or purposes. Examples of non-transitory computer-readable media include, but are not limited to, magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which may include, for example, the instructions and/or computer code disclosed herein.

The systems, devices, and/or methods described herein may be performed by software (executed on hardware), hardware, or a combination thereof. Hardware modules may include, for example, a general-purpose processor (or microprocessor or microcontroller), a field programmable gate array (FPGA), and/or an application specific integrated circuit (ASIC). Software modules (executed on hardware) may be expressed in a variety of software languages (e.g., computer code), including C, C++, Java®, Ruby, Visual Basic®, and/or other object-oriented, procedural, or other programming language and development tools. Examples of computer code include, but are not limited to, micro-code or micro-instructions, machine instructions, such as produced by a compiler, code used to produce a web service, and files containing higher-level instructions that are executed by a computer using an interpreter. Additional examples of computer code include, but are not limited to, control signals, encrypted code, and compressed code.

The specific examples and descriptions herein are exemplary in nature and embodiments may be developed by those skilled in the art based on the material taught herein without departing from the scope of the present invention.

The invention claimed is:

1. An apparatus, comprising:
   a memory; and
   a processor operatively coupled to the memory, the processor configured to:
   receive cardiac signal data captured by a set of electrodes;
   extract a sliding window of the cardiac signal data;
   process data from the extracted sliding window;
   identify a peak frequency over a subrange of frequencies associated with the processed data from the extracted sliding window by:
      performing a discrete Fourier transform of the processed data from the extracted sliding window;
      filtering the discrete Fourier transform of the processed data to produce filtered Fourier transform data; and
      identifying from the filtered Fourier transform data the peak frequency as the frequency over the subrange of frequencies having an amplitude in the filtered Fourier transform data that is larger than that of the remaining frequencies in the subrange of frequencies;
   detect ectopic activity based at least on a measure of the peak frequency over the subrange of frequencies; and
   in response to detecting ectopic activity, send an indication of ectopic activity to a signal generator configured to generate pulsed waveforms for cardiac ablation.

2. The apparatus of claim 1, wherein the processor is configured to send the indication of ectopic activity to the signal generator such that the signal generator is deactivated from generating the pulsed waveforms.

3. The apparatus of claim 1, wherein the processor is further configured to:
   process the cardiac signal data by:
      amplifying and filtering the cardiac signal data; and
      digitizing the cardiac signal data; and
   buffer the processed cardiac signal data in the memory,
   the processor configured to extract the sliding window from the buffered cardiac signal data.

4. The apparatus of claim 1, wherein the processor is configured to detect ectopic activity by:
   calculating a ratio of the amplitude of the peak frequency over the subrange of frequencies to a maximum amplitude of frequencies up to the Nyquist frequency of the frequency output;
   determining whether the ratio is greater than a threshold value; and
   detecting the ectopic activity based on determining that the ratio is greater than the threshold value.

5. The apparatus of claim 4, wherein the threshold value is between about 0.01 and about 0.25.

6. The apparatus of claim 4, wherein the threshold value is between about 0.01 and about 0.15.

7. The apparatus of claim 4, wherein the processor is operatively coupled to a user interface, and the threshold value is set by a user via the user interface.

8. An apparatus, comprising:
   a memory; and
   a processor operatively coupled to the memory, the processor configured to:
   receive cardiac signal data captured by a set of electrodes;
   process the cardiac signal data by:
      amplifying and filtering the cardiac signal data; and
      digitizing the cardiac signal data;
   buffer the processed cardiac signal data in the memory;
   receive an indication of delivery of a set of pacing pulses to the cardiac tissue;
   extract portions of the cardiac signal data from the buffered cardiac signal data following delivery of a subset of successive pacing pulses from the set of pacing pulses, each extracted portion of the cardiac signal data including cardiac signal data within a predetermined time interval following an onset of a pacing pulse from the subset of successive pacing pulses;
   calculate, for each extracted portion, a set of moments of a function associated with that extracted portion;
   confirm pacing capture of the set of pacing pulses based at least on the set of moments calculated for each extracted portion; and
   in response to confirming pacing capture, send an indication of pacing capture to a signal generator configured to generate pulsed waveforms for cardiac ablation such that the signal generator is activated for generating the pulsed waveforms.

9. The apparatus of claim 8, wherein the predetermined time interval is between about 5 milliseconds and about 50 milliseconds.

10. The apparatus of claim 8, wherein the processor is configured to confirm pacing capture by:
    calculating, for each moment from the set of moments, an average value of that moment by averaging values of the moments calculated for the extracted portions;
    calculating, for each moment from the set of moments, a normalized difference between the average value of that moment and the value of that moment calculated for each extracted portion; and
    confirming pacing capture based on the normalized differences calculated for each moment from the set of moments.

11. The apparatus of claim 8, wherein the processor is configured to confirm pacing capture by:
    calculating average values of each of the set of moments;
    calculating normalized differences between the average values of each of the set of moments and the values of the moments calculated for the extracted portions; and
    determining when each normalized difference is less than a respective predetermined threshold.

12. The apparatus of claim 8, wherein the processor is further configured to:
analyze local peak frequencies of the cardiac signal data to detect ectopic activity; and
in response to detecting ectopic activity, send an indication of ectopic activity to the signal generator such that the signal generator is deactivated from generating the pulsed waveforms.

13. The apparatus of claim 12, wherein the processor is configured to analyze the local peak frequencies of the cardiac signal data to detect ectopic activity by:
extracting sliding windows of the cardiac signal data;
performing discrete Fourier transforms of the extracted sliding windows and applying a filter to the resulting discrete Fourier transforms to produce filtered frequency outputs of the extracted sliding windows;
identifying the local peak frequencies in the filtered frequency outputs; and
detecting ectopic activity based at least on amplitudes of the peak frequencies in the filtered frequency outputs.

14. A system, comprising:
a first controller configured to generate a pulsed waveform and deliver the pulsed waveform in synchrony with a set of pacing pulses to an ablation device; and
a second controller operatively coupled to the first controller, the second controller configured to:
generate the set of pacing pulses and deliver the set of pacing pulses to a pacing device;
receive cardiac signal data captured by a set of electrodes;
confirm pacing capture of the set of pacing pulses based on the cardiac signal data; and
in response to confirming pacing capture, send an indication of pacing capture to the first controller to activate generation of the pulsed waveform.

15. The system of claim 14, wherein the pacing device includes a pair of electrodes for pacing a chamber of a heart and the set of electrodes for capturing the cardiac signal data.

16. The system of claim 14, wherein the second controller is further configured to send an indication of the set of pacing pulses to the first controller such that the first controller can deliver the pulsed waveform in synchrony with the set of pacing pulses.

17. The system of claim 14, wherein the second controller is configured to confirm pacing capture by:
extracting portions of the cardiac signal data following delivery of a subset of successive pacing pulses from the set of pacing pulses;
calculate, for each extracted portion, a set of moments of a function associated with that extracted portion; and
confirm pacing capture of the set of pacing pulses based at least on the set of moments calculated for each extracted portion.

18. The system of claim 17, wherein each extracted portion of the cardiac signal data includes cardiac signal data within a predetermined time interval following an onset of a pacing pulse from the subset of successive pacing pulses.

19. The system of claim 14, wherein the second controller is further configured to:
monitor the cardiac signal data for ectopic activity; and
when ectopic activity is present, send an indication of ectopic activity to the first controller to deactivate generation of the pulsed waveform.

20. The system of claim 19, wherein the second controller is configured to monitor for ectopic activity by:
extracting sliding windows of the cardiac signal data following delivery of each pacing pulse from the set of pacing pulses;
performing discrete Fourier transform of the extracted sliding windows and applying a filter to the resulting discrete Fourier transform to produce filtered frequency outputs of the extracted sliding windows; and
analyzing peak frequencies over a subrange of frequencies in the filtered frequency outputs.

21. The system of claim 19, wherein the second controller is operatively coupled to a user interface, the second controller further configured to, when ectopic activity is present, cause the user interface to display an alert indicating that ectopic activity is present.

22. A method, comprising:
receiving cardiac signal data captured by a set of electrodes disposed near cardiac tissue;
extracting a sliding window of the cardiac signal data;
process data from the extracted sliding window;
identifying a peak frequency over a subrange of frequencies associated with the processed data from the extracted sliding window by:
performing a discrete Fourier transform of the processed data from the extracted sliding window;
filtering the discrete Fourier transform of the processed data to produce filtered Fourier transform data; and
identifying from the filtered Fourier transform data the peak frequency as the frequency over the subrange of frequencies having an amplitude in the filtered Fourier transform data that is larger than that of the remaining frequencies in the subrange of frequencies;
detecting ectopic activity based at least on a measure of the peak frequency over the subrange of frequencies; and
in response to detecting ectopic activity, sending an indication of ectopic activity to a signal generator configured to generate pulsed waveforms for cardiac ablation such that the signal generator is deactivated from generating the pulsed waveforms.

23. The method of claim 22, wherein detecting ectopic activity includes:
calculating a ratio of the amplitude of the peak frequency over the subrange of frequencies to a maximum amplitude of frequencies up to the Nyquist frequency of the frequency output;
determining whether the ratio is greater than a threshold value; and
detecting the ectopic activity based on determining that the ratio is greater than the threshold value.

24. The method of claim 23, wherein the threshold value is between about 0.01 and about 0.15.

25. The method of claim 22, further comprising:
confirming pacing capture of the set of pacing pulses based on the cardiac signal data.

* * * * *